(12) United States Patent
Hsu et al.

(10) Patent No.: US 10,295,449 B2
(45) Date of Patent: May 21, 2019

(54) DETERMINING RESONANCE FREQUENCY AND QUALITY FACTOR

(71) Applicant: Schlumberger Technology Corporation, Sugar Land, TX (US)

(72) Inventors: Kai Hsu, Sugar Land, TX (US); Florian Risser, Elancourt (FR); Gocha Chochua, Sugar Land, TX (US); Haitao Zhang, Sugar Land, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 447 days.

(21) Appl. No.: 14/574,381

(22) Filed: Dec. 17, 2014

(65) Prior Publication Data

US 2016/0177707 A1   Jun. 23, 2016

(51) Int. Cl.
| | | |
|---|---|---|
| *G01N 9/00* | (2006.01) | |
| *E21B 47/10* | (2012.01) | |
| *G01N 11/16* | (2006.01) | |
| *G01N 29/036* | (2006.01) | |
| *G01N 29/22* | (2006.01) | |
| *G01N 29/44* | (2006.01) | |

(52) U.S. Cl.
CPC ............. *G01N 9/002* (2013.01); *E21B 47/10* (2013.01); *G01N 11/16* (2013.01); *G01N 29/036* (2013.01); *G01N 29/222* (2013.01); *G01N 29/4418* (2013.01); *G01N 29/4472* (2013.01); *G01N 2009/006* (2013.01); *G01N 2291/012* (2013.01); *G01N 2291/015* (2013.01); *G01N 2291/02491* (2013.01); *G01N 2291/02818* (2013.01)

(58) Field of Classification Search
CPC ............. G01N 9/002; G01N 2009/006; G01N 2291/02818; G01N 29/222; G01N 29/4472; G01N 29/4418; G01N 11/16
See application file for complete search history.

(56) References Cited

U.S. PATENT DOCUMENTS

| | | | |
|---|---|---|---|
| 7,874,199 B2 | 1/2011 | Chaudoreille et al. | |
| 7,958,772 B2 | 6/2011 | Permuy et al. | |
| 2009/0120171 A1* | 5/2009 | Harrison | G01N 11/16 73/64.53 |

OTHER PUBLICATIONS

Daungkaew et al., Is There a Better Way to Determine the Viscosity in Waxy Crudes?, Oct. 22-24, 2012, SPE 159337, SPE Asia Pacific Oil and Gas Conference and Exhibition, Perth, Australia, 11 pp.*

* cited by examiner

Primary Examiner — Toan M Le

(57) ABSTRACT

Methods and apparatus for obtaining data from a density-viscosity (DV) sensor of a downhole tool, wherein the DV sensor comprises a resonating element disposed in a fluid flowing in a flowline of the downhole tool, and determining a resonance frequency and quality factor of the resonating element utilizing a nonlinear regression and/or a plurality of resonance modes exhibited by the obtained data.

20 Claims, 13 Drawing Sheets

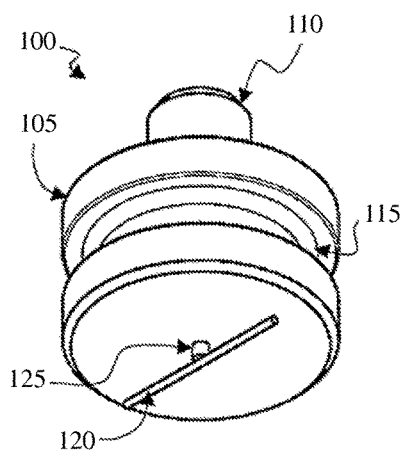
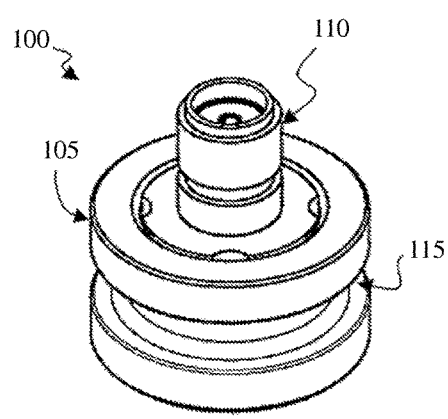
FIG. 1                FIG. 2
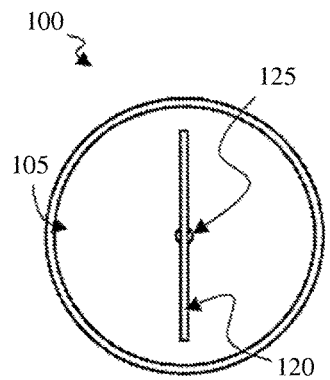
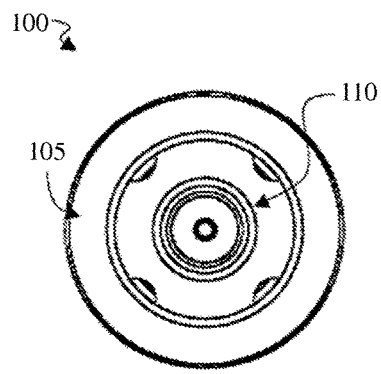
FIG. 3                FIG. 4

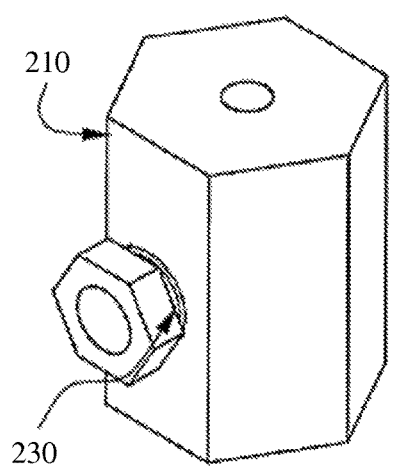
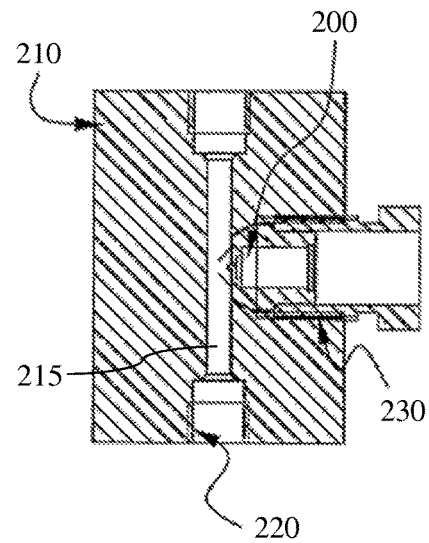
*FIG. 10*  *FIG. 11*
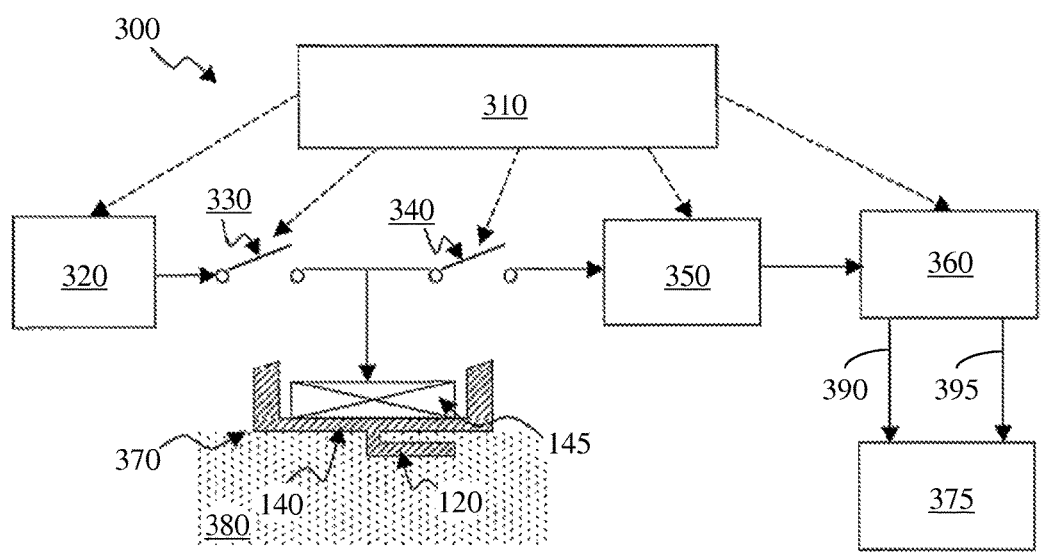
*FIG. 12*

DETERMINING RESONANCE FREQUENCY AND QUALITY FACTOR

BACKGROUND OF THE DISCLOSURE

Existing density and viscosity sensors measure density and viscosity of a subterranean formation fluid downhole. Such sensors operate based on the principle of a mechanically vibrating and resonating element interacting with the formation fluid flowing within a flowline of the downhole tool. The sensors measure the mechanical resonance of the resonating element vibrating in the fluid flowing in the flowline, outputting voltage-versus-time data that conforms to a simple damped harmonic model. The data is processed to determine the resonance frequency and quality factor, from which the density and viscosity of the fluid may be determined.

SUMMARY OF THE DISCLOSURE

This summary is provided to introduce a selection of concepts that are further described below in the detailed description. This summary is not intended to identify indispensable features of the claimed subject matter, nor is it intended for use as an aid in limiting the scope of the claimed subject matter.

The present disclosure introduces a method that includes obtaining data from a density-viscosity (DV) sensor of a downhole tool. The DV sensor includes a resonating element disposed in a fluid flowing in a flowline of the downhole tool. The method also includes determining a resonance frequency and quality factor of the resonating element based on a primary resonance mode and a secondary resonance mode exhibited in the obtained data.

The present disclosure also introduces an apparatus that includes a downhole tool and surface equipment. The downhole tool is operable within a wellbore extending from a wellsite surface into a subterranean formation. The downhole tool includes a flowline for conducting fluid obtained from the subterranean formation via operation of the downhole tool, and a density-viscosity (DV) sensor that includes a resonating element disposed in the flowline. The surface equipment is disposed at the wellsite surface and is in communication with the downhole tool. At least one of the downhole tool and the surface equipment is operable to obtain data from the DV sensor and determine a resonance frequency and quality factor of the resonating element based a primary resonance mode and a secondary resonance mode exhibited in the obtained data.

The present disclosure also introduces a method that includes obtaining data from a density-viscosity (DV) sensor of a downhole tool. The DV sensor includes a resonating element disposed in a fluid flowing in a flowline of the downhole tool. The method also includes determining from the obtained data a resonance frequency and quality factor of the resonating element utilizing a nonlinear regression.

These and additional aspects of the present disclosure are set forth in the description that follows, and/or may be learned by a person having ordinary skill in the art by reading the materials herein and/or practicing the principles described herein. At least some aspects of the present disclosure may be achieved via means recited in the attached claims.

BRIEF DESCRIPTION OF THE DRAWINGS

The present disclosure is understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

FIG. 1 is a perspective view of at least a portion of apparatus according to one or more aspects of the present disclosure.

FIG. 2 is another perspective view of the apparatus shown in FIG. 1.

FIG. 3 is an end view of the apparatus shown in FIGS. 1 and 2.

FIG. 4 is another end view of the apparatus shown in FIGS. 1-3.

FIG. 10 is a perspective view of at least a portion of an example implementation of apparatus according to one or more aspects of the present disclosure.

FIG. 11 is a sectional view of the apparatus shown in FIG. 10.

FIG. 12 is a schematic view of at least a portion of an example implementation of apparatus according to one or more aspects of the present disclosure.

DETAILED DESCRIPTION

Figure 5:
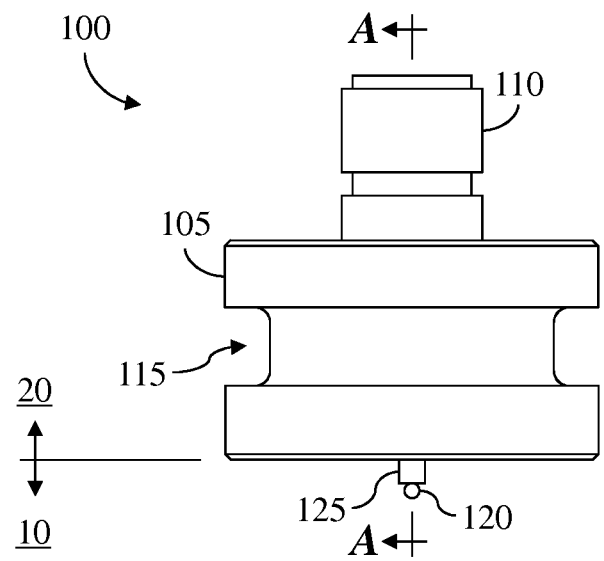
FIG. 5 is a side view of the apparatus shown in FIGS. 1-4.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for simplicity and clarity, and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

FIG. 1 is a perspective view of at least a portion of an example implementation of a density-viscosity (DV) sensor 100 according to one or more aspects of the present disclosure. FIG. 2 is another perspective view of the DV sensor 100 shown in FIG. 1. FIG. 3 is an end view of a fluid contacting side (FCS) 10 of the DV sensor 100 shown in FIGS. 1 and 2. FIG. 4 is an end view of a sensor connecting side (SCS) 20 of the DV sensor 100 shown in FIGS. 1-3. FIG. 5 is a side view of the DV sensor 100 shown in FIGS. 1-4. The following description refers to FIGS. 1-5, collectively.

The DV sensor 100 comprises a housing 105, such as may be formed of high strength and high corrosion resistance stainless steel, for example. The housing 105 comprises a standardized coaxial (coax) connector or other type of connector 110. The housing 105 may comprise a groove 115 for receiving an O-ring type seal (not shown) that may aid in fluidly isolating the FCS 10 from the SCS 20. The FCS 10 may be exposed to high pressure, high temperature, corrosive fluid, and/or an otherwise harsh environment, whereas the SCS 20 may be at atmospheric pressure and/or otherwise isolated from the harsh environment of the FCS 10.

The DV sensor 100 also comprises a resonating element 120 coupled to the housing 105 by a mechanical coupling 125. The resonating element 120 is depicted in FIGS. 1, 3, and 5 as a single beam attached to the housing 105 by the mechanical coupling 125. For example, the resonating element 120 be or comprise a wire having a substantially cylindrical, elliptical, or otherwise shaped cross-section, perhaps having a diameter less than about ten micrometers (μm), although other cross-sectional shapes and/or dimensions are also within the scope of the present disclosure. The resonating element 120 may be made of a high strength and high corrosion resistance material, such as stainless steel, or a material with low density, such as sapphire or boron carbon. The resonating element 120 may instead be made of specific materials for detecting or measuring chemical species in the fluid.

The mechanical coupling 125 may be an integral part of the housing 105 to which the resonating element 120 is coupled. However, the mechanical coupling 125 may instead be an integral part of the resonating element 120, or may be or comprise one or more discrete members coupled between the housing 105 and the resonating element 120. In each such implementation, the mechanical coupling 125 mechanically couples the housing 105 to the resonating element 120 such that vibration is transmitted between the housing 105 and the resonating element 120 through the mechanical coupling 125. For example, the mechanical coupling 125 may be coupled to the housing 105 and/or the resonating element 120 via welding, adhesive, brazing, and/or other means by which vibration may be transferred between the housing 105 and the resonating element 120. The mechanical coupling 125 also positions the resonating element 120 in a fluid to be measured (not shown), such that the resonating element 120 is surrounded by and/or immersed in the fluid.

Figure 6:
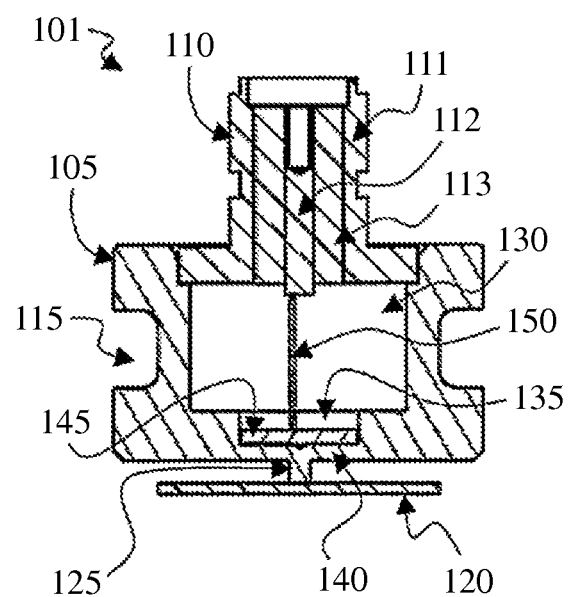
FIG. 6 is a sectional view of an example implementation of the apparatus shown in FIGS. 1-5.

FIG. 6 is a sectional view of an example implementation of the DV sensor 100 shown in FIG. 5, taken along lines A-A as depicted in FIG. 5, and designated in FIG. 6 by reference numeral 101. The housing 105 may comprise a chamber 130 and a cavity 135. The cavity 135 may define an area where the housing 105 has a reduced thickness defining a membrane 140 between the chamber 130 and the FCS 10. The mechanical coupling 125 may be positioned on the membrane 140. For example, the mechanical coupling 125 may be positioned at substantially a center point on the membrane 140. The chamber 130 may be filled with a material, such as gas, oil, gel, and/or other vibration absorbing materials that may aid in reducing reduce perturbations due to parasitic vibration modes of the housing 105. The chamber 130 may be sealed via assembly of the connector 110 to the housing 105.

A piezoelectric and/or other actuating/detecting element 145 is positioned in the cavity 135. One side of the actuating/detecting element 145 is coupled to the connector 110 by one or more wires and/or other conductors 150, and the other side of the actuating/detecting element 145 is electrically coupled to the membrane 140. In such implementations, among others, the actuating/detecting element 145 may substantially operate in extension.

The actuating/detecting element 145 may comprise one or more metal layers (not shown) substantially covering each side. Thus, the electrical connection between the actuating/detecting element 145 and the membrane 140 may be via conductive adhesive, brazing, and/or other electrically conductive means. However, the actuating/detecting element 145 may also or instead be mechanically secured against the membrane 140, such as via one or more threaded fasteners, clips, interference/press fit, and/or other means.

The connector 110 may comprise an external portion 111, an internal portion 112, and an intermediate portion 113. The external portion 111 may be electrically conductive, and may be in contact with the housing 105. The internal portion 112 may be electrically conductive, and may be electrically connected to the one or more conductors 150. The intermediate portion 113 may comprise an electrically insulating material, and may electrically isolate the external and internal portions 111, 112 of the connector 110. Thus, the actuating/detecting element 145 may be excited by an appropriate electrical signal applied between its two sides, namely on one side by the external portion 111 and the housing 105, and on the other side by the internal portion 112 and the one or more conductors 150.

Figure 7:
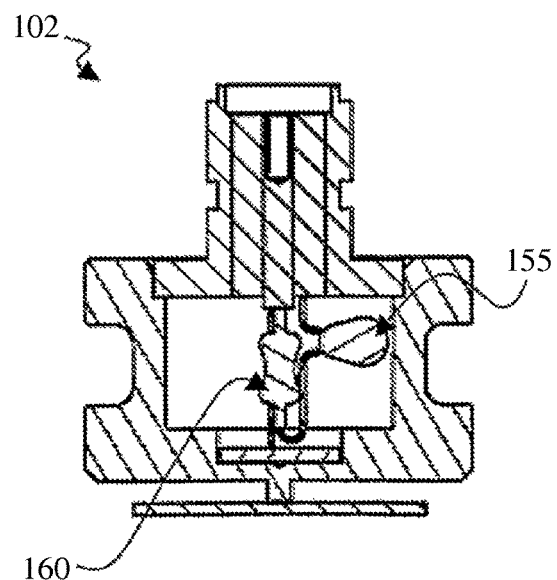
FIG. 7 is a sectional view of another example implementation of the apparatus shown in FIGS. 1-5.

FIG. 7 is a sectional view of another example implementation of the DV sensor 100 shown in FIG. 5, again taken along lines A-A as depicted in FIG. 5, and designated in FIG. 7 by reference numeral 102. The DV sensor 102 shown in FIG. 7 is substantially similar to or the same as the DV sensor 101 shown in FIG. 6, with the following possible exceptions.

For example, a thermistor 155 may be positioned within the chamber 130 of the housing 105. The thermistor 155 may be utilized to measure temperature at the position where the DV measurement is being performed. The thermistor 155 may also be connected to a resistance 160 for adapting the range of temperature measurement to the particular application for which the DV sensor 102 is intended to be used. The temperature measurement may be utilized to compensate for temperature effects on the DV measurements. The thermistor 155 is an example means for measuring temperature, however, and other temperature-measuring arrangements (e.g., a diode) may also or instead be utilized.

Figure 8:
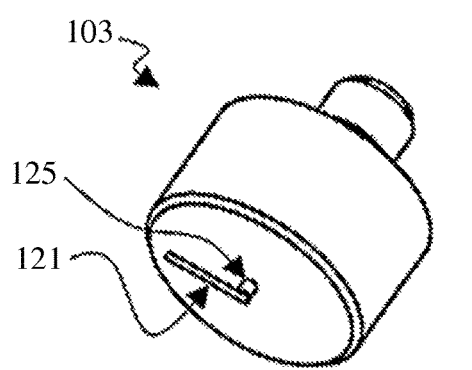
FIG. 8 is a perspective view of another example implementation of the apparatus shown in FIGS. 1-5.

FIG. 8 is a perspective view of another example implementation of the DV sensor 100 shown in FIGS. 1-5, designated in FIG. 8 by reference numeral 103. The DV sensor 103 shown in FIG. 8 is substantially similar to or the same as the DV sensor 101 shown in FIGS. 1, 3, and 5, with the following possible exception. That is, FIG. 8 depicts a resonating element 121 that is substantially similar to or the same as the resonating element 120 shown in FIGS. 1, 3, and 5, except that an end of the resonating element 121 shown in FIG. 8 is attached to the mechanical coupling 125, in contrast to the example implementation shown in FIGS. 1, 3, and 5 in which the midpoint of the resonating element 120 is attached to the mechanical coupling 125.

Figure 9:
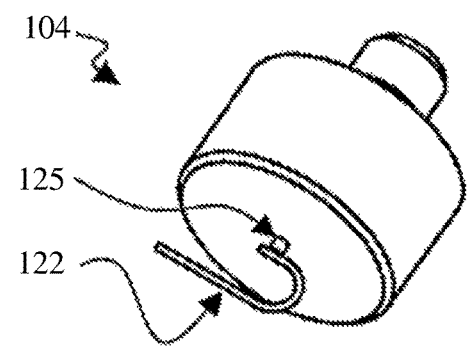
FIG. 9 is a perspective view of another example implementation of the apparatus shown in FIGS. 1-5.

FIG. 9 is a perspective view of another example implementation of the DV sensor 100 shown in FIGS. 1-5, designated in FIG. 9 by reference numeral 104. The DV sensor 104 shown in FIG. 9 is substantially similar to or the same as the DV sensor 101 shown in FIGS. 1, 3, and 5, with the following possible exception. That is, FIG. 9 depicts a resonating element 122 that is substantially similar to or the same as the resonating element 120 shown in FIGS. 1, 3, and 5, except that the resonating element 122 shown in FIG. 9 is a non-symmetrical, at least partially U-shaped member. In the example implementation depicted in FIG. 9, the resonating element 122 comprises a first longitudinal portion for contacting the fluid to be measured (not shown), and a second curved portion attached by one end to the mechanical coupling 125. However, other related implementations are also within the scope of the present disclosure.

In the example implementations depicted in FIGS. 1, 3, and 5-9, the resonating element 120, 121, 122 may be aligned with the direction of fluid flow, whether in an upstream or downstream orientation. Such implementations may aid in reducing erosion of the resonating element 120, 121, 122 in high velocity fluid flow. Such implementations may also or instead aid in reducing turbulence induced by the presence of the resonating element 120, 121, 122 in the fluid flow and, thus, the otherwise resulting measurement noise.

Moreover, the scope of the present disclosure is not limited to implementations utilizing the resonating element depicted in one or more of FIGS. 1, 3, and 5-9. For example, the resonating element may comprise multiple members oriented in a cross, star, or other design.

The DV sensors described above may also comprise means for installation to a conduit, tube, pipe, or other portion of a downhole tool. For example, FIG. 10 is a perspective view of a portion of an example implementation in which a DV sensor 200 is installed in a conduit 210. FIG. 11 is a sectional view of the apparatus shown in FIG. 10. The following description refers to FIGS. 10 and 11, collectively.

The DV sensor 200 is, or is at least substantially similar to, one or more of the DV sensors 100-104 shown in one or more of FIGS. 1-9. The conduit 210 is depicted as having a substantially hexagonal shaped cross-section, although otherwise shaped conduit are also within the scope of the present disclosure.

The conduit 210 comprises a connection 220 for coupling to a main conduit or pipe. The DV sensor 200 is fitted into a threaded housing 230. The conduit 210 comprises a threaded opening (not numbered) for receiving the threaded housing 230. The threaded opening may comprise an abutment such that, when the threaded housing 230 is installed, the resonating element 200 is adequately positioned relative to a flowline 215 extending within the conduit 210.

FIG. 12 is a schematic view of at least a portion of an example implementation of an electronic arrangement 300 according to one or more aspects of the present disclosure, representing an example application in which a DV sensor as described above may be utilized. For the sake of example, the following description refers to a DV sensor 370 that is substantially similar to or the same as one or more of the DV sensors 100-104, 200 shown in one or more of FIGS. 1-11.

At least a portion of the electronic arrangement 300 may be implemented within the DV sensor 370, such as within the chamber 130 shown in FIG. 6. However, at least a portion of the electronic arrangement 300 may instead be externally coupled to a connector of the DV sensor 370, such as the connector 110 shown in FIGS. 1-9. The electronic arrangement 300 may be implemented by a number of discrete electronic components, or at least a portion of the electronic arrangement 300 may be implemented as one or more integrated circuits.

The electronic arrangement 300 may comprise a controlling circuit 310, an oscillator 320, a first switch 330, a second switch 340, an amplifier 350, a detection circuit 360, and a processing circuit 375. The controlling circuit 310 is in electrical communication with the oscillator 320, the first switch 330, the second switch 340, the amplifier 350, and the detection circuit 360 via various electrical connections (not shown) known in the art.

The oscillator 320 may be or comprise a sweep oscillator and/or other means for performing a sensor excitation and detection scheme described below. During operation, the controlling circuit 310 may close the first switch 330 and open the second switch 340, such that the oscillator 320 may apply an excitation signal to the actuating/detecting element 145. The excitation signal application causes the actuating/detecting element 145 to apply and relax strain to the membrane 140 and to the resonating element 120 by virtue of their mutual mechanical coupling. The excitation signal may be on the order of one volt, such as less than about ten volts.

After a vibration has been established by exciting the actuating/detecting element 145, the excitation may be removed and a reception signal representative of the vibration of the resonating element 120 in the fluid 380 may be measured. Thereafter, the controlling circuit 310 may close the second switch 340 and open the first switch 330, and the actuating/detecting element 145 may generate a reception signal representative of the strain variation of the membrane 140 mechanically coupled to the resonating element 120. The amplifier 350 may amplify the detection signal. The detection circuit 360 may perform a synchronous detection during a detection phase, and may provide to the processing circuit 375 an actual in-phase response signal 390 and an actual quadrature response signal 395 measured by the DV sensor 370.

The detection signal may include or be indicative of a voltage corresponding to the resonance response of the resonating element 120. The voltage response v(t) conforms to a simple damped harmonic model as set forth below in Equation (1).

$$v(t) = A e^{-\alpha \omega t} \sin(\omega t + \phi) \quad (1)$$

where A is the amplitude of the initial transient, a is the logarithmic decrement controlling the damping of the motion, ω is the resonance frequency of the resonating element 120 (in radian/sec), t is the time index, and φ is the unknown phase angle. In Equation (1), the logarithmic decrement α is related to the quality factor Q as set forth below in Equation (2).

$$\alpha = 1/2Q \quad (2)$$

During operation, the detection signal may be processed to determine the resonance frequency ω and quality factor Q. Using the determined resonance frequency ω and quality factor Q, one can then determine the density and viscosity of the fluid 380 fluid surrounding the resonating element 120 based on working equations. Assuming the model of Equation (1), the processing may compute the coherence between the acquired data and the model prediction. The resonance frequency and quality factor may be determined by locating the values of ω and Q that maximize the computed coherence function.

However, in addition to the primary resonance mode (i.e., transverse mode), the acquired data also includes the secondary resonance mode (i.e., lateral mode) with its resonance frequency higher than that of the primary resonance mode. The secondary resonance mode is excited because its resonance frequency is within the bandwidth of the excitation pulse. Therefore, by assuming there is merely one mode in the data, the above-described processing may provide an erroneous estimate of resonance frequency ω and quality factor Q. Moreover, the actuating/detecting element 145 of the DV sensor 370 is used for actuating and receiving the vibration of the resonating element 120, such that the acquired data at the beginning of operations contains some degree of baseline drift similar to that of a capacitor-discharging effect from excitation. As a result, the above-described processing may exclude the initial data during this "settling period" because the model (i.e., Equation (1)) and the above-described processing do not account for the drift. Unfortunately, for high viscosity fluid, it is often the data obtained during the settling period that contains the resonance data of interest. This result may impose limitations to the operating range of the fluid. However, the present disclosure introduces one or more aspects by which such issues may be circumvented to obtain a reliable estimate of resonance frequency and quality factor.

For example, the model of Equation (1), which solely considers the response of the primary resonance mode, can be modified to account for the secondary mode, as set forth below in Equation (3).

$$v(t) = A_1 e^{-\alpha_1 \omega_1 t} \sin(\omega_1 t + \phi_1) + A_2 e^{-\alpha_2 \omega_2 t} \sin(\omega_2 t + \phi_2) \quad (3)$$

where $A_1$ is the amplitude of the initial transient of the primary resonance mode, $\alpha_1$ is the logarithmic decrement controlling damping of motion of the resonating element 120 relative to the primary resonance mode, $\omega_1$ is the resonance frequency of the resonating element 120 relative to the primary resonance mode, $\phi_1$ is the unknown phase angle of the primary resonance mode, $A_2$ is the amplitude of the initial transient of the secondary resonance mode, $\alpha_2$ is the logarithmic decrement controlling damping of motion of the resonating element 120 relative to the secondary resonance mode, $\omega_2$ is the resonance frequency of the resonating element 120 relative to the secondary resonance mode, and $\phi_2$ is the unknown phase angle of the secondary resonance mode.

The primary and secondary resonance modes may be acquired via operation of an implementation of one or more of the DV sensors described above, such as by causing an excitation and then acquiring the response data. For example, a first excitation and data acquisition cycle may be performed to acquire the response relative to the primary resonance mode, and then a second excitation and data acquisition may be performed to acquire the response relative to the secondary resonance mode. However, a single excitation and data acquisition cycle may also or instead be performed to acquire the response relative to both of the primary and second resonance modes simultaneously. Processing the primary and second resonance modes simultaneously may aid in reducing the total acquisition time by providing a single excitation at a frequency between the modes and performing a single, simultaneous processing of the primary and second resonance modes. One or more excitation and data acquisition cycles may also or instead be performed to acquire one or more responses relative to more than two resonance modes.

In this context, the model of Equations (1) and (3) may also be adapted to account for a general number n of resonance modes, as set forth below in Equation (3.1).

$$v(t) = \Sigma_{i=1}^{i=n} A_i e^{-\alpha_i \omega_i t} \sin(\omega_i t + \phi_i) \quad (3.1)$$

where the number n of resonance nodes is greater than or equal to one, $A_i$ is the amplitude of the initial transient of the $i^{th}$ resonance mode, $\alpha_i$ is the logarithmic decrement controlling damping of motion of the resonating element 120 relative to the $i^{th}$ resonance mode, $\omega_i$ is the resonance frequency of the resonating element 120 relative to the $i^{th}$ resonance mode, and $\phi_i$ is the unknown phase angle of the $i^{th}$ resonance mode.

Moreover, the unknown background drift and offset that may be present in the data can be accounted for as set forth below in Equation (4).

$$v(t) = A_1 e^{-\alpha_1 \omega_1 t} \sin(\omega_1 t + \phi_1) + A_2 e^{-\alpha_2 \omega_2 t} \sin(\omega_2 t + \phi_2) + A_3 e^{-\sigma t} + a \quad (4)$$

where a is an additional unknown constant that characterizes the offset, and where $A_3$ and $\sigma$ account for time-drift (e.g., capacitor discharging effect) due to unknown background interference. It is noted, however, that other suitable models (i.e., polynomial models) may also or instead be utilized to characterize the unknown background interference.

As above, the model of Equation (4) may also be adapted to account for a general number n of resonance modes, as set forth below in Equation (4.1).

$$v(t) = \Sigma_{i=1}^{i=n} A_i e^{-\alpha_i \omega_i t} \sin(\omega_i t + \phi_i) + B e^{-\sigma t} + a \quad (4.1)$$

where B and σ account for time-drift (e.g., capacitor discharging effect) due to unknown background interference.

Determination of ω and Q according to one or more aspects of the present disclosure utilizes data fitting with Equation (4) or (4.1). For example, it is noted that the method of least-squares-fitting is based on the idea that the optimum characterization of a set of data is one that minimizes the sum of the squares of the deviation of the data from the fitting model (i.e., Equation (4) or (4.1)). The sum of the squares of the deviation is closely related to the goodness-of-fit statistic called chi-square (or $\chi^2$), as set forth below in Equation (5).

$$\chi^2 = \frac{\sum_{i=1}^{N} |V(t_i) - v(t_i)|^2}{\nu} \quad (5)$$

where $t_i$ is the time index, $V(t_i)$ and $v(t_i)$ are the recorded voltage data and the modeled response based on Equation (4) or (4.1), respectively, and $\nu$ is the number of degrees of freedom for fitting N data points. The least squares criterion is formulated as finding the unknown parameters to minimize the chi-square defined in Equation (5), such as set forth below in Equation (6).

$$\min_{A_1, \omega_1, \alpha_1, \phi_1, A_2, \omega_2, \alpha_2, \phi_2, A_3, \sigma, a} \chi^2 \quad (5)$$

where $A_1$, $\omega_1$, $\alpha_1$, $\phi_1$, $A_2$, $\omega_2$, $\alpha_2$, $\phi_2$, $A_3$, $\sigma$, and $a$ are the unknown parameters. The inputs to the nonlinear fitting (or regression) are the recorded data V(t), and the output of the fitting are estimated parameters listed above.

The nonlinear fitting may be achieved with the Levenberg-Marquardt iteration, which provides an iterative procedure to solve for this minimization, as set forth below in Equation (7).

$$p_{k+1} = p_k + (J(p_k)^T J(p_k) + \lambda_k I)^{-1} J(p_k)^T (V - v(p_k)) \quad (7)$$

where $p_k$ is the parameter vector (which contains each of the unknown parameters defined in Equation (6)) at the $i^{th}$ iteration, I is the identity matrix, $\lambda_k$ is the Marquardt parameter, and $J(p_k)$ is the Jacobian matrix defined as set forth below in Equation (8).

$$J(p_k) = \frac{\partial}{\partial p}(V - v(p))\bigg|_{p=pk} \quad (8)$$

In this case, the Jacobian matrix $J(p_k)$, which involves taking the derivatives with respect to p, is easy to compute because the analytical form of derivatives for this problem is readily available. Note that when $\lambda_k \to 0$, the iteration in Equation (7) is equivalent to the Gauss-Newton method and, in contrast, when $\lambda_k$ becomes a large number, Equation (7) approaches the steepest descent method. Thus, $\lambda_k$ is initially set to 0.001. If $\chi^2$ from Equation (6) is reduced after an iteration, then $\lambda_k$ is reduced by a factor of ten. Otherwise, $\chi^2$ is increased by a factor of ten. As a minimum of Equation (6) is approached, $\lambda_k$ will become very small, and the Gauss-Newton method converges to the solution. On the other hand, when the parameter vector $p_k$ is far away from the minimum, $\lambda_k$ is set to a large number, and the iteration switches to the steepest descent method, which ensures the reduction of $\chi^2$ in Equation (6) in the subsequent iteration.

Figure 13:
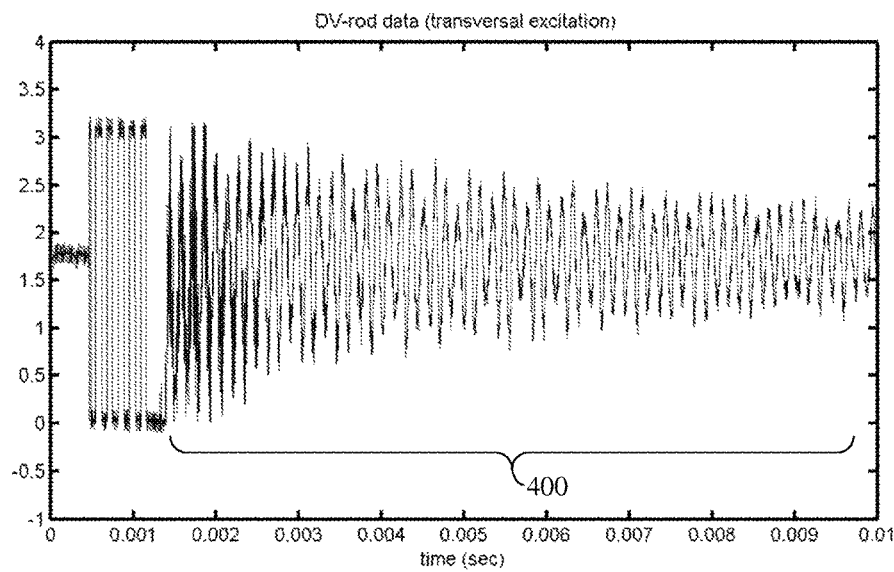
FIG. 13 is a chart depicting an example of voltage-versus-time data related to one or more aspects of the present disclosure.
Figure 14:
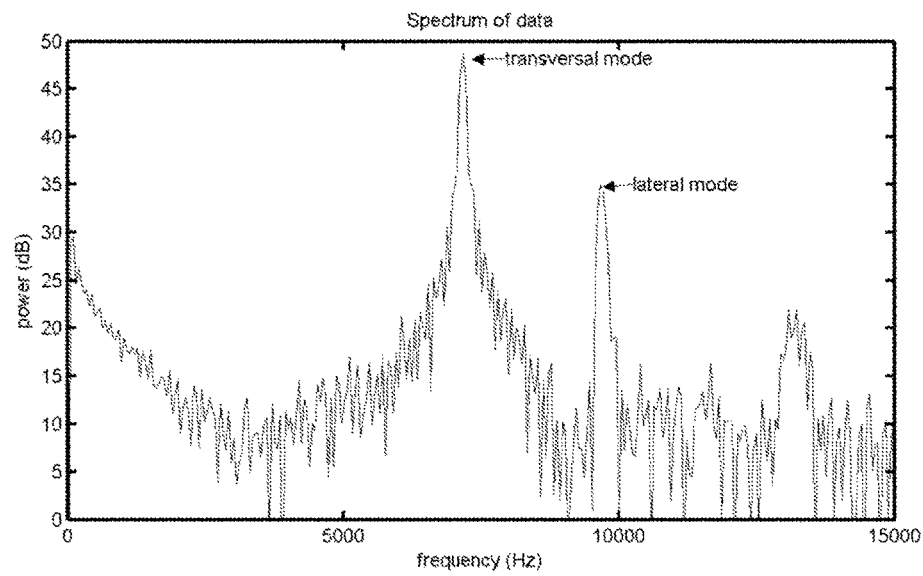
FIG. 14 is a chart depicting example power-versus-frequency of the data shown in FIG. 13.
Figure 15:
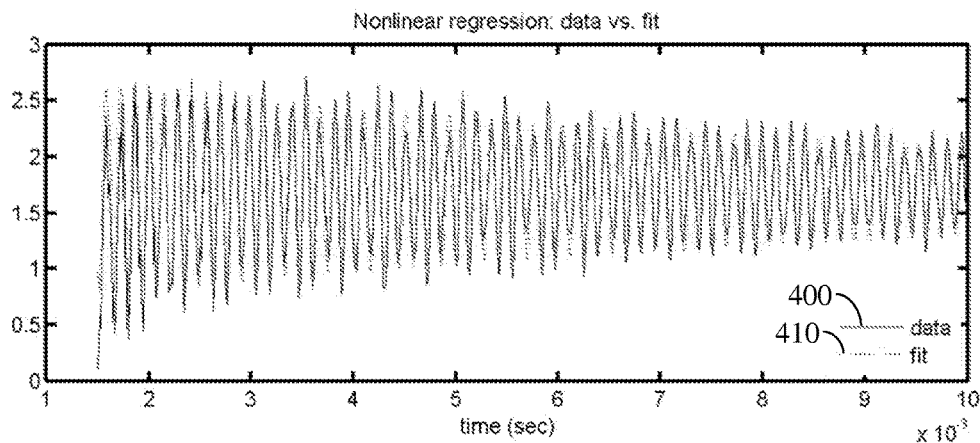
FIG. 15 is a chart depicting a portion of the data shown in FIG. 13 and a corresponding single-mode fit.
Figure 16:
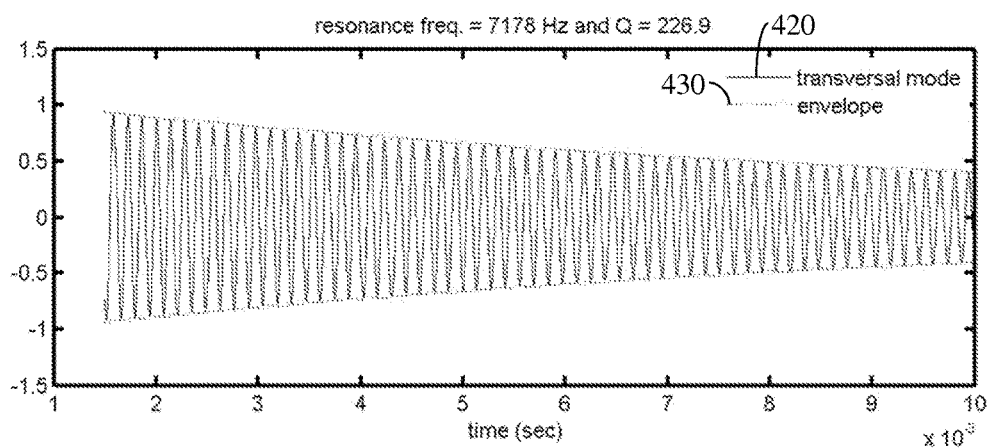
FIG. 16 is a chart depicting a transversal mode of the data shown in FIG. 15.
Figure 17:
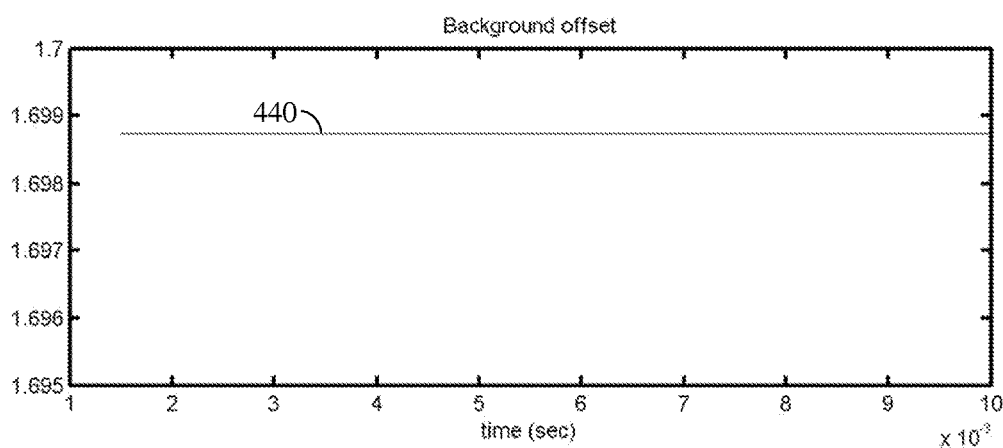
FIG. 17 is a chart depicting background offset of the data shown in FIG. 15.

FIG. 13 is a chart demonstrating one or more aspects of the present disclosure via example data acquired with a transversal excitation in a known fluid. FIG. 14 is an associated power spectrum of a portion 400 of the acquired data shown in FIG. 13. As depicted in FIG. 14, the data 400 include two resonance modes: one around 7 kHz (transversal mode) and the other around 9.5 kHz (lateral mode). FIGS. 15-17 are charts depicting the results of nonlinear regression using the single-mode model with offset, as set forth above in Equation (1).

For example, FIG. 15 depicts the portion 400 of the data (solid line) overlaid with the single-mode best fit 410 (dotted line). Such overlay illustrates noticeable disagreement between the data 400 and the single-mode best fit 410. FIG. 16 is an associated chart depicting the estimated transversal mode 420 and corresponding envelope 430. FIG. 17 is an associated chart depicting the estimated background offset 440. In the example depicted in FIGS. 15-17, the estimated resonance frequency is 7178 Hz and the quality factor is 226.9.

Figure 18:
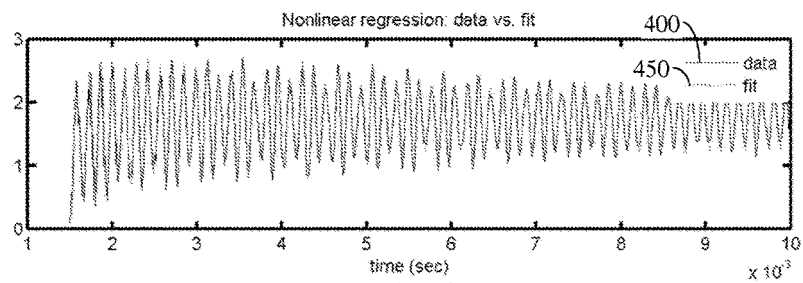
FIG. 18 is a chart depicting a portion of the data shown in FIG. 13 and a corresponding dual-mode fit.
Figure 19:
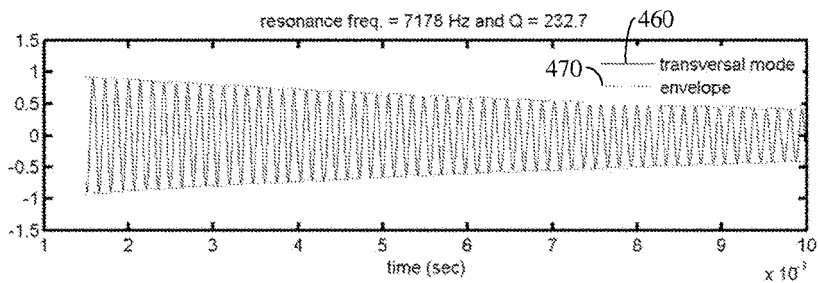
FIG. 19 is a chart depicting a transversal mode of the data shown in FIG. 18.
Figure 20:
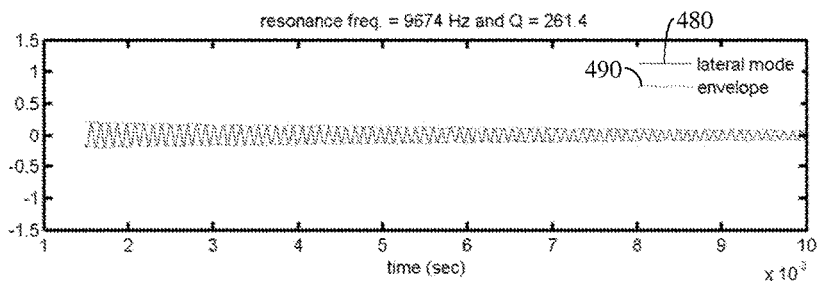
FIG. 20 is a chart depicting a lateral mode of the data shown in FIG. 18.
Figure 21:
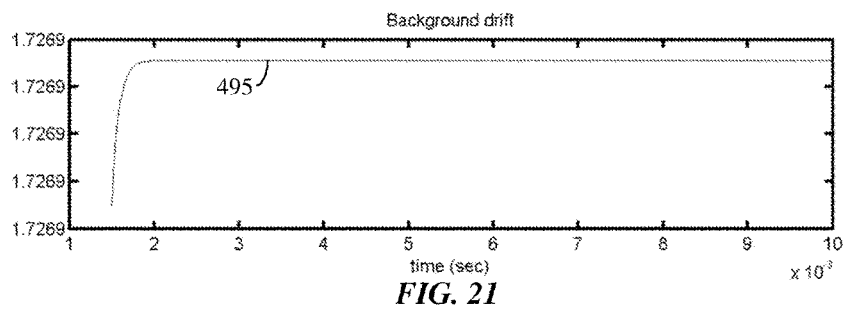
FIG. 21 is a chart depicting background offset of the data shown in FIG. 18.

FIG. 18 is a chart depicting the associated results of nonlinear regression using the dual-mode model set forth above in Equation (4) or (4.1). As shown in FIG. 18, substantially greater agreement exists between the data 400 and the dual-mode best fit 450. The substantially greater agreement is attributable, at least in part, to the fact that the data 400 actually contain two resonance modes that are properly fitted with the dual-mode model, thus permitting both the transversal mode 460 (within corresponding envelope 470) and the lateral mode 480 (within corresponding envelope 490) to be resolved, as shown in FIGS. 19 and 20, respectively. As a result, the estimated resonance frequency and quality factor of each mode, as labeled in the corresponding figures, is substantially more accurate than the results obtained with the single-mode model. FIG. 21 is also presented to illustrate the associated background drift 495 with respect to time.

Figure 22:
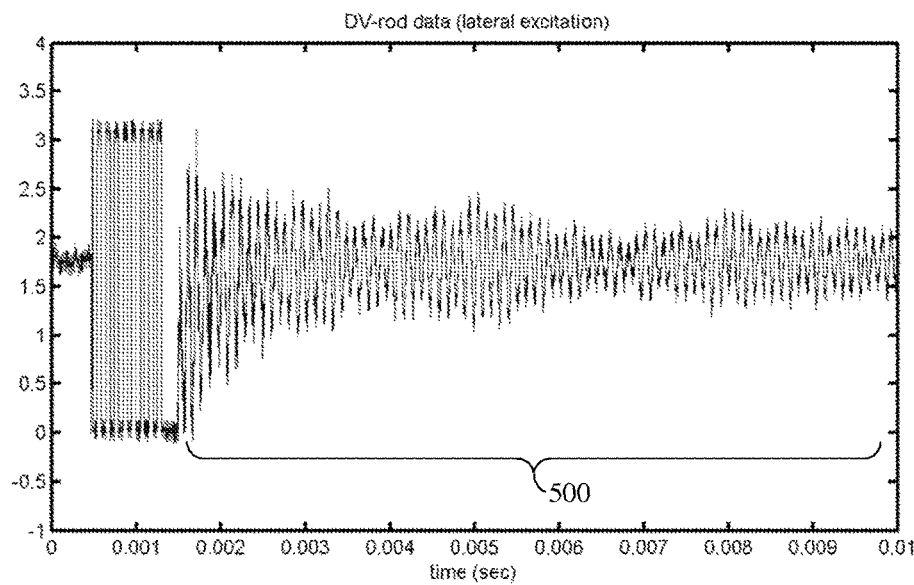
FIG. 22 is a chart depicting another example of voltage-versus-time data related to one or more aspects of the present disclosure.
Figure 23:
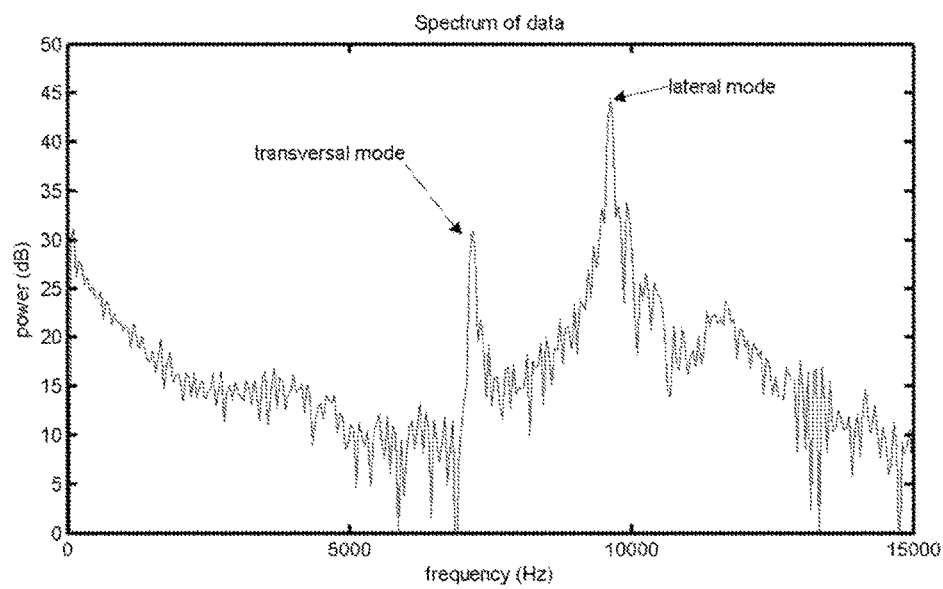
FIG. 23 is a chart depicting example power-versus-frequency of the data shown in FIG. 22.
Figure 24:
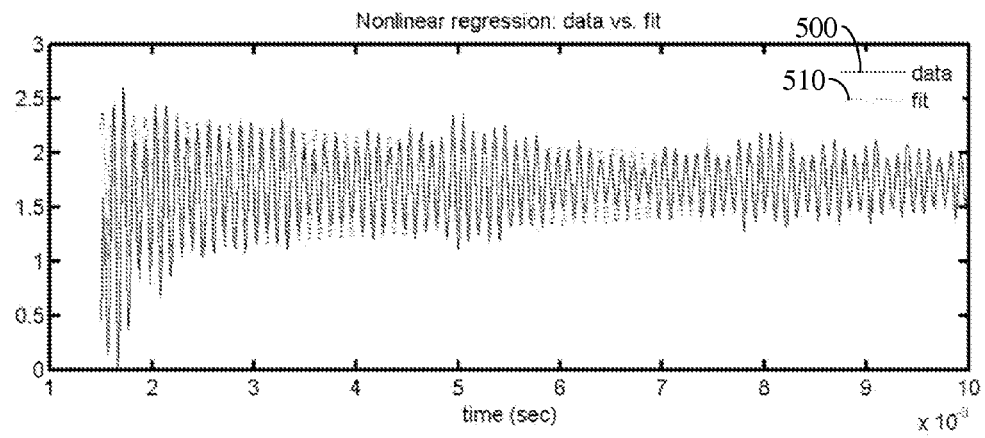
FIG. 24 is a chart depicting a portion of the data shown in FIG. 22 and a corresponding single-mode fit.
Figure 25:
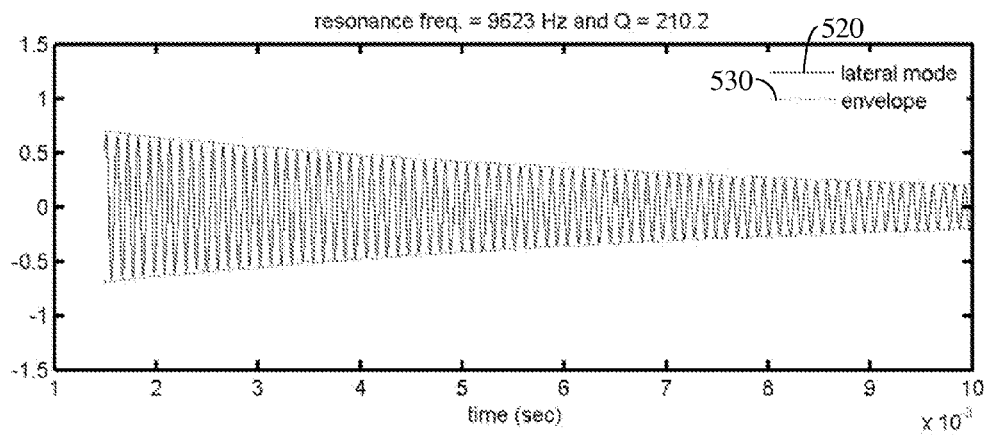
FIG. 25 is a chart depicting a lateral mode of the data shown in FIG. 24.
Figure 26:
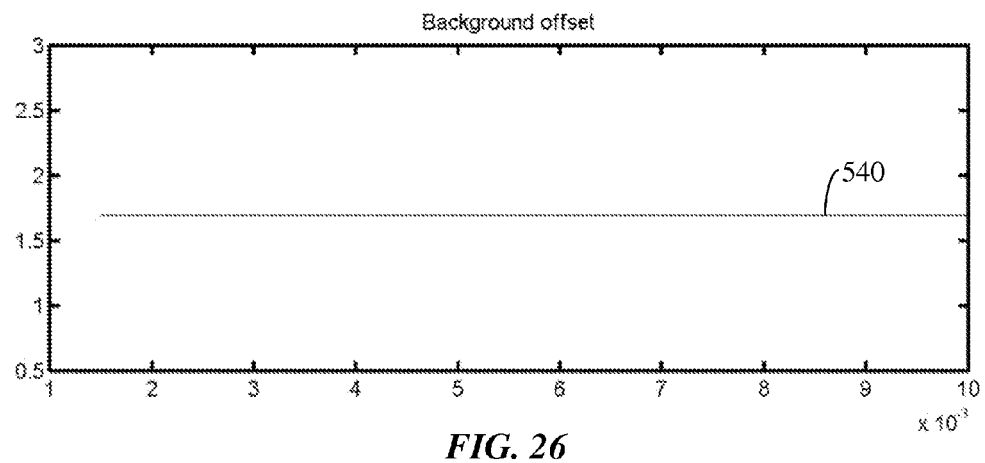
FIG. 26 is a chart depicting background offset of the data shown in FIG. 24.

FIG. 22 is a chart demonstrating one or more aspects of the present disclosure via example data acquired with a lateral excitation in a known fluid. FIG. 23 is an associated power spectrum of a portion 500 of the acquired data shown in FIG. 22. As depicted in FIG. 23, the data 500 include two resonance modes: one around 7 kHz (transversal mode) and the other around 9.5 kHz (lateral mode). FIGS. 24-26 are charts depicting the results of nonlinear regression using the single-mode model with offset, as set forth above in Equation (1).

For example, FIG. 24 depicts the portion 500 of the data (solid line) overlaid with the single-mode best fit 510 (dotted line). Such overlay illustrates noticeable disagreement between the data 500 and the single-mode best fit 510, such that a reliable estimate of resonance frequency and quality factor would not be expected. FIG. 25 is an associated chart depicting the estimated transversal mode 520 and corresponding envelope 530. FIG. 17 is an associated chart depicting the estimated background offset 540. In this example, the estimated resonance frequency is 9623 Hz and the quality factor is 210.2.

Figure 27:
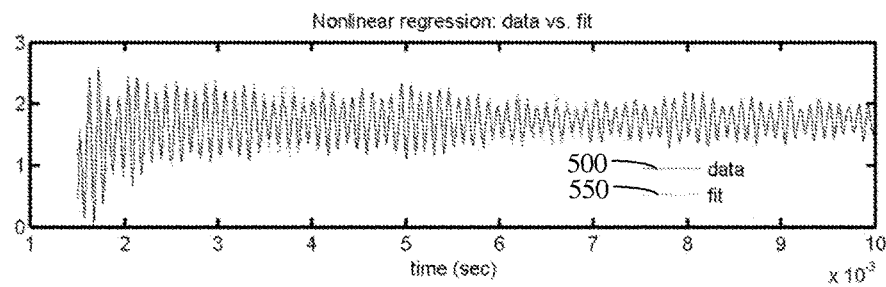
FIG. 27 is a chart depicting a portion of the data shown in FIG. 22 and a corresponding dual-mode fit.
Figure 28:
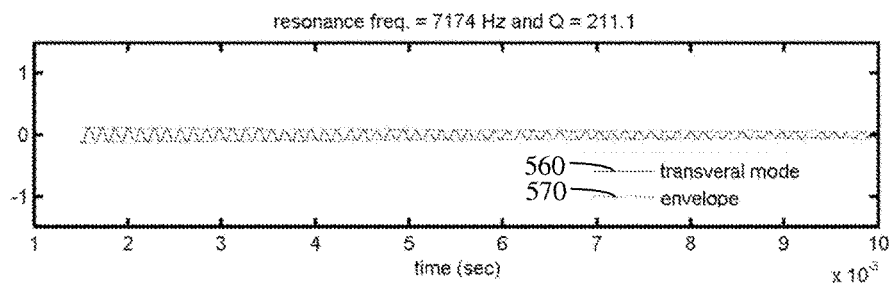
FIG. 28 is a chart depicting a transversal mode of the data shown in FIG. 27.
Figure 29:
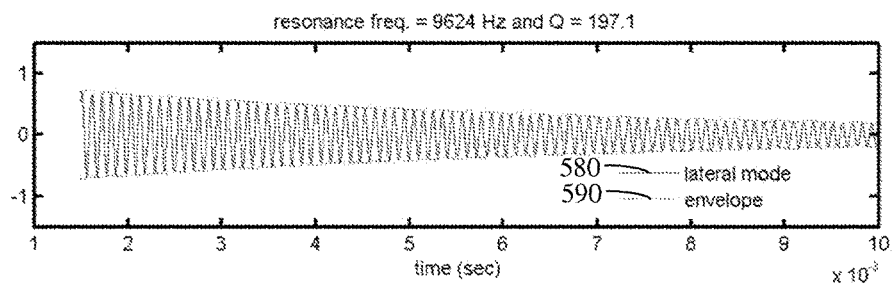
FIG. 29 is a chart depicting a lateral mode of the data shown in FIG. 27.
Figure 30:
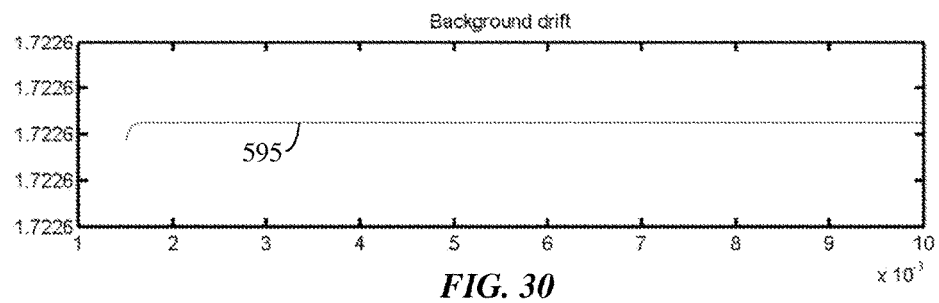
FIG. 30 is a chart depicting background offset of the data shown in FIG. 27.

FIG. 27 is a chart depicting the associated results of nonlinear regression using the dual-mode model set forth above in Equation (4) or (4.1). As shown in FIG. 27, substantially greater agreement exists between the data 500 and the dual-mode best fit 550. As above, the substantially greater agreement is attributable, at least in part, to the fact that the data 500 actually contain two resonance modes that are properly fitted with the dual-mode model, thus permitting both the transversal mode 560 (within corresponding envelope 570) and the lateral mode 580 (within corresponding envelope 590) to be resolved, as shown in FIGS. 28 and 29, respectively. As a result, the estimated resonance frequency and quality factor of each mode, as labeled in the corresponding figures, is substantially more accurate than the results obtained with the single-mode model. FIG. 30 is also presented to illustrate the associated background drift 595 with respect to time.

Table 1 set forth below summarizes the results of these two examples. Among other aspects notable in Table 1 is the substantial drop in $\chi^2$ relative between the single-mode fitting and the dual-mode fitting, such as may provide an indication of an improved goodness-of-fit using the dual-mode model.

TABLE 1

|  |  | Transversal mode | | Lateral mode | | |
|---|---|---|---|---|---|---|
|  |  | Freq. (Hz) | Q | Freq. (Hz) | Q | $\chi$ |
| Transverse Excitation (FIGS. 13-21) | Single-mode | 7178 | 226.9 | N/A | N/A | 0.109 |
|  | Dual-mode | 7178 | 232.7 | 9674 | 261.4 | 0.047 |
| Lateral Excitation (FIGS. 22-30) | Single-mode | N/A | N/A | 9623 | 210.2 | 0.254 |
|  | Dual-mode | 7174 | 211.1 | 9624 | 197.1 | 0.103 |

After obtaining the resonance frequency and quality factor utilizing the dual-mode model as described above, the density $\rho$ and viscosity $\eta$ of the fluid may be obtained based on the obtained resonance frequency and quality factor utilizing known methods. For example, the density $\rho$ and viscosity $\eta$ may be determined as set forth below in Equations (9) and (10).

$$\rho = \rho_R \left( K \left( \frac{\omega_V}{\omega_F} \right)^2 - 1 \right) \left( FIT0 + FIT1 \left( 1 - \left( \frac{\omega_F}{\omega_V} \right)^2 \frac{1}{K} \right)^{-1} \left( \frac{1}{Q} - \frac{1}{Q_V} \right) \right) \quad (9)$$

$$\eta = \frac{\rho_R \omega_V^2 K R^2}{\omega_F \sqrt{K} \left( \frac{1}{Q} - \frac{1}{Q_V} \right)^{-2} \left( 1 - \left( \frac{\omega_F}{\omega_V} \right)^2 \frac{1}{K} \right)} \quad (10)$$

$$\left( FIT2 + FIT3 \left( 1 - \left( \frac{\omega_1}{\omega_V} \right) \frac{1}{K} \right)^{-1} \left( \frac{1}{Q_1} - \frac{1}{Q_V} \right) \right)$$

where $\rho_R$ is the density of the resonating element 120, $\omega_F$ and $\omega_V$ are the resonance frequency of the fluid currently measured and the resonance frequency in vacuum or air, Q and $Q_V$ are the quality factor currently measured and the associated quality factor in vacuum or air, FIT0, FIT1, FIT2, and FIT3 are fitting parameters that may be determined by measuring the resonance frequencies and quality factors in fluids of known density and viscosity, R is the characteristic dimension of the resonating element 120, and K is a correction factor representing the shift of the Young's modulus of the material of the resonating element 120 due to variation of pressure and temperature with respect to a pressure and temperature condition when measuring $\omega_V$ and $Q_V$ (K may also be affected by a shift in the electronics reference frequency due to temperature or aging).

The correction factor K may be determined as set forth below in Equation (11).

$$K = \frac{FIT10 - FIT20}{\left( \left( \frac{\omega_1}{\omega_V} \right)^2 \left( FIT10 - FIT11 \left( \frac{1}{Q_1} - \frac{1}{Q_{1V}} \right) \right) \right) - \left( \left( \frac{\omega_{2V}}{\omega_2} \right)^2 \left( FIT20 - FIT21 \left( \frac{1}{Q_2} - \frac{1}{Q_{2V}} \right) \right) \right)} \quad (11)$$

where FIT10, FIT11, FIT20, and FIT21 are fitting parameters that may be determined by measuring the resonance frequencies and quality factors in fluids of known density and viscosity.

Figure 31:
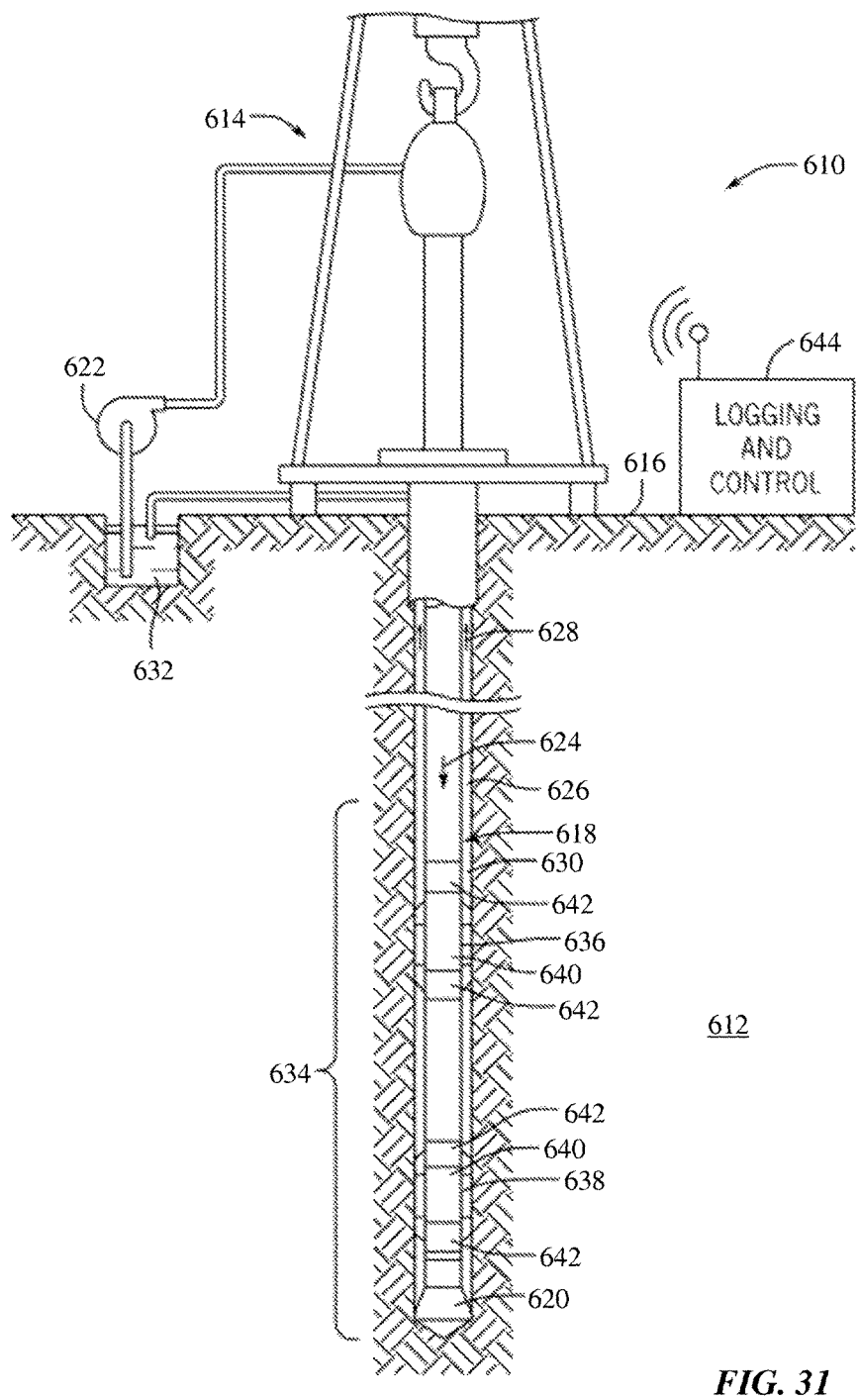
FIG. 31 is a schematic view of at least a portion of an example implementation of apparatus according to one or more aspects of the present disclosure.

FIG. 31 is a schematic view of at least a portion of a drilling system 610 operable to drill a wellbore 626 into one or more subsurface formations 12. A drilling rig 614 at the wellsite surface 616 is operable to rotate a drill string 618 that includes a drill bit 620 at its lower end. As the drill bit 620 is rotated, a pump 622 pumps drilling fluid (commonly referred to as "mud" or "drilling mud") downward through the center of the drill string 618 in the direction of arrow 624 to the drill bit 620. The mud, which is utilized to cool and lubricate the drill bit 620, exits the drill string 618 through ports (not shown) in the drill bit 620. The mud then carries drill cuttings away from the bottom of the wellbore 626 as it flows back to the wellsite surface 616 through an annulus 630 between the drill string 618 and the formation 612, as shown by arrows 628. At the wellsite surface 616, the return mud is filtered and conveyed back to a mud pit 632 for reuse.

While a drill string 618 is illustrated in FIG. 31, it will be understood that the embodiments described herein may be applicable or readily adaptable to work strings and wireline tools as well. Work strings may include a length of tubing (e.g., coiled tubing) lowered into the wellbore 626 for conveying well treatments or well servicing equipment. Wireline tools may include formation testing tools suspended from a multi-conductor cable as the cable is lowered into the wellbore 626 to measure formation properties at desired depths. The location and environment of the drilling system 610 may vary widely depending on the formation 612 penetrated by the wellbore 626. Instead of being a surface operation, for example, the wellbore 626 may be formed under water of varying depths, such as on an ocean bottom surface. Certain components of the drilling system 610 may be specially adapted for underwater wells in such instances.

The lower end of the drill string 618 includes a bottom-hole assembly (BHA) 634, which includes the drill bit 620 and a plurality of drill collars 636, 638. The drill collars 636, 638 may include various instruments, such as sample-while-drilling (SWD) tools that include sensors, telemetry equipment, and so forth. For example, the drill collars 636, 638 may include one or more logging-while-drilling (LWD) modules or other tools 640, and/or measurement-while-drilling (MWD) modules or other tools 642. The LWD modules or tools 640 may be operable to measure formation parameters and/or fluid properties, such as resistivity, porosity, permeability, sonic velocity, OD, pressure, temperature, and/or others. For example, the LWD modules or tools 640 may be operable for determining resonance frequency and/or quality factor according to one or more aspects described above. The MWD modules or tools 642 may be operable to measure wellbore trajectory, borehole temperature, borehole pressure, and so forth. The LWD and/or MWD modules or tools 640, 642 may each be housed in one of the drill collars 636, 638, and may include capabilities for measuring, processing, and/or storing information, as well as for communicating with each other and/or directly with the surface equipment such as, for example, a logging and control unit 644, disposed at the wellsite surface 616. That is, the LWD and/or MWD modules or tools 640, 642 may be communicatively coupled to the logging and control unit 644. However, some portions of the logging and control unit 644 may be integrated with downhole features.

The LWD and/or MWD modules or tools 640, 642 may include a downhole formation fluid sampling tool operable to selectively sample fluid from the formation 612. The drilling system 610 may be operable to determine, estimate, or otherwise obtain various properties associated with the sampled formation fluid, such as the resonance frequency and/or quality factor described above. These and/or other properties may be determined within or communicated to the logging and control unit 644, such as for subsequent utilization as input to various control functions and/or data logs.

Figure 32:
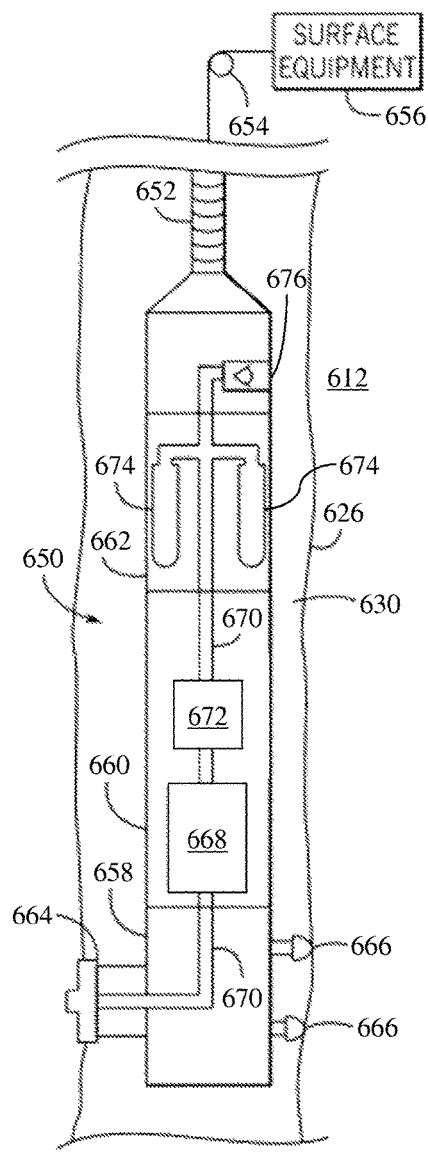
FIG. 32 is a schematic view of at least a portion of an example implementation of apparatus according to one or more aspects of the present disclosure.

FIG. 32 is a schematic diagram of an example implementation of downhole equipment operable to sample fluid from a formation, such as the formation(s) 612 shown in FIG. 31. Referring to FIGS. 31 and 32, collectively, the downhole equipment includes an example implementation of a downhole formation fluid sampling tool 650, hereinafter referred to as the downhole tool 650. The downhole tool 650 is conveyable within the wellbore 626 to the subsurface formation 612 and subsequently operable to sample formation fluid from the formation 612. In the implementation depicted in FIG. 32, the downhole tool 650 is conveyed in the wellbore 626 via a wireline 652, but the downhole tool 650 could also be one of the LWD and/or MWD modules or tools 640, 642 shown in FIG. 31.

The downhole tool 650 may be suspended in the wellbore 626 from a lower end of the wireline 652, which may be a multi-conductor cable spooled from a winch 654. The wireline 652 may be electrically coupled to wellsite surface equipment 656, such as to communicate various control signals and logging information between the downhole tool 650 and the wellsite surface equipment 656. The wellsite surface equipment 656 shown in FIG. 32 and the logging and control unit 644 shown in FIG. 31, or functions thereof, may be integrated in a single system at the wellsite surface 616.

The downhole tool 650 includes a probe module 658, a pumpout module 660, and a sample module 662, one or more of which may comprise, be part of, or be substantially similar to one or more of the LWD and/or MWD modules or tools 640, 642 shown in FIG. 31. However, other arrangements and/or modules may make up the downhole tool 650.

The probe module 658 may comprise an extendable fluid communication line (probe 664) operable to engage the formation 612 and communicate fluid samples from the formation 612 into the downhole tool 650. The probe module 658 may also comprise one or more setting mechanisms 666. The setting mechanisms 666 may include pistons and/or other apparatus operable to improve sealing engagement and thus fluid communication between the formation 612 and the probe 664. The probe module 658 may also comprise one or more packer elements (not shown) that inflate or are otherwise operable to contact an inner wall of the wellbore 626, thereby isolating a section of the wellbore 626 for sampling. The probe module 658 may also comprise electronics, batteries, sensors, and/or hydraulic components used, for example, to operate the probe 664 and the corresponding setting mechanisms 666.

The pumpout module 660 may comprise a pump 668 operable to create a pressure differential that draws the formation fluid in through the probe 664 and pushes the fluid through a flowline 670 of the downhole tool 650. The pump 668 may comprise an electromechanical, hydraulic, and/or other type of pump operable to pump formation fluid from the probe module 658 to the sample module 662 and/or out of the downhole tool 650. The pump 668 may operate as a piston displacement unit (DU) driven by a ball screw coupled to a gearbox and an electric motor, although other types of pumps 668 are also within the scope of the present disclosure. Power may be supplied to the pump 668 via other components located in the pumpout module 660, or via a separate power generation module (not shown). During a sampling period, the pump 668 moves the formation fluid through the flowline 670 toward the sample module 662.

The pumpout module 660 may also include a DV sensor 672 operable to measure characteristics of the formation fluid as it flows through the flowline 670, as described above with respect to the DV sensors 100-104 shown in one or more of FIGS. 1-9, among other implementations within the scope of the present disclosure. The DV sensor 672 may be located downstream or upstream of the pump 668. The characteristics sensed by the DV sensor 672 may include resonance frequency, quality factor, density, and/or viscosity of the formation fluid, among other examples. Data collected via the DV sensor 672 may be utilized to control the downhole tool 650. For example, the downhole tool 650 may not operate in a sampling mode until the formation fluid flowing through the flowline 670 exhibits characteristics of a clean formation fluid sample, as detected by or otherwise determined in conjunction with operation of the DV sensor 672 and/or other sensors of the downhole tool 650. A clean formation fluid sample contains a relatively low level of contaminants (e.g., drilling mud filtrate) that are miscible with the formation fluid when extracted from the formation 612.

The sample module 662 may comprise one or more sample bottles 674 for collecting samples of the formation fluid. Based on the measured, sensed, and/or otherwise determined characteristics of the formation fluid detected via sensors (e.g., the DV sensor 672) along the flowline 670, the downhole tool 650 may be operated in a sampling mode or a continuous pumping (cleanup) mode. When operated in the sampling mode, valves (not shown) disposed at or near entrances of the sample bottles 674 may be positioned to permit the formation fluid to flow into the sample bottles 674. The sample bottles 674 may be filled one at a time, and once a sample bottle 674 is filled, its corresponding valve may be moved to another position to seal the sample bottle 674. When the valves are closed, the downhole tool 650 may operate in a continuous pumping mode. An implementation of the DV sensors described above may be disposed within one or more of the sample bottles 674, whether in addition to or instead of the DV sensor being disposed along the flowline 670, such that the resonance frequency, quality factor, density, and/or viscosity of formation fluid disposed in the sample bottle 674 may be determined according to one or more aspects of the present disclosure.

In the continuous pumping mode, the pump 668 moves the formation fluid into the downhole tool 650 through the probe 664, through the flowline 670, and then out of the downhole tool 650 through an exit port 676. The exit port 676 may be a check valve that releases the formation fluid into the annulus 630 of the wellbore 626. The downhole tool 650 may operate in the continuous pumping mode until the formation fluid flowing through the flowline 670 is determined to be clean enough for sampling. That is, when the formation fluid is first sampled, drilling mud filtrate that has been forced into the formation 612 via the drilling operations may enter the downhole tool 650 along with the sampled formation fluid. After pumping the formation fluid for an amount of time, the formation fluid flowing through the downhole tool 650 will provide a cleaner fluid sample of the formation 612 than would otherwise be available when first drawing fluid in through the probe 664. For example, the formation fluid may be considered clean when the data from the DV sensor 672 and/or other sensors of the downhole tool 650 indicate that the formation fluid contains less than approximately 1%, 5%, or 10% filtrate contamination (by volume), although other values are also within the scope of the present disclosure.

The characteristics of the formation fluid measured by the DV sensor 672 may be useful for performing a variety of evaluation and control functions, in addition to determining when the formation fluid flowing through the flowline 670 is clean enough for sampling. For example, data may be collected from the DV sensor 672 and/or other sensors within the downhole tool 650, such as a pressure sensor, a temperature sensor, a saturation pressure sensor, and/or an optical spectrometer, among others. The collected data may be utilized to estimate a formation volume factor of the contaminated formation fluid, as well as density, optical density, GOR, compressibility, saturation pressure, viscosity, and/or mass fractions of compositional components of the contaminated formation fluid and/or contaminants therein (e.g., OBM filtrate), among others.

Figure 33:
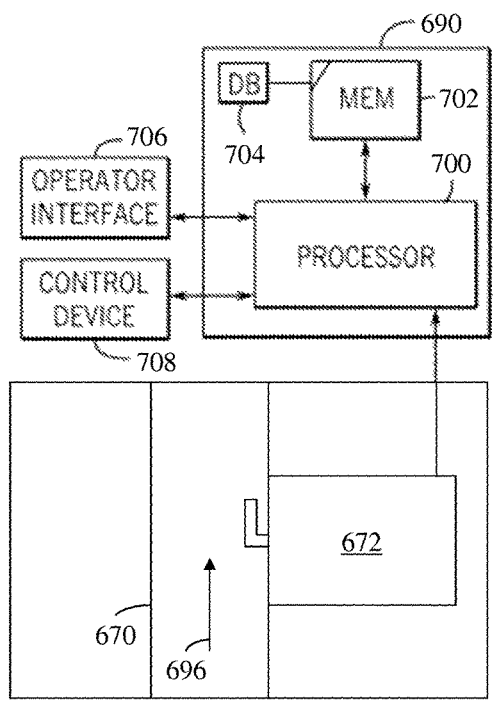
FIG. 33 is a schematic view of a portion of the apparatus shown in FIG. 32.

FIG. 33 is a schematic diagram of the DV sensor 672 and a control/monitoring system 690 may be utilized to estimate or determine such properties. The DV sensor 672 may be on a side of the flowline 670 through which the formation fluid flows, as indicated by arrow 696, such as in a manner that may be at least similar to the arrangement depicted in the example implementations shown in FIGS. 10-12. The DV sensor 672 may be part of the downhole tool 650, and may be located at various possible locations along the flowline 670 that directs the formation fluid through the downhole tool 650.

The DV sensor 672 may measure one or more characteristics of the formation fluid flowing through the flowline 670 and output data representative of the detected characteristics. The DV sensor 672 may send data representative of the measured characteristics to a processor 700 of the control/monitoring system 690. In the context of the present disclosure, the term "processor" refers to any number of processor components. The processor 700 may include a single processor disposed onboard the downhole tool 650. In other implementations, at least a portion of the processor 700 (e.g., multiple processors collectively operating as the processor 700) may be located within the wellsite surface equipment 656 of FIG. 32, the logging and control unit 644 of FIG. 31, and/or other surface equipment components. The processor 700 may also or instead be or include one or more processors located within the downhole tool 650 and connected to one or more processors located in drilling and/or other equipment disposed at the wellsite surface 616. Moreover, various combinations of processors may be considered part of the processor 700 in the following discussion. Similar terminology is applied with respect to the control/monitoring system 690 as well as a memory 702 of the control/monitoring system 690, meaning that the control/monitoring system 690 may include various processors communicatively coupled to each other and/or various memories at various locations.

The control/monitoring system 690 may estimate the resonance frequency, quality factor, density, viscosity, and/or other characteristics of the formation fluid based on the data received from the DV sensor 672, a pressure sensor, a temperature sensor, and/or other sensors, and may utilize the estimated characteristics to determine GOR, mass fractions of compositional components, and/or other properties of the formation fluid. To make these and other determinations, the processor 700 may execute instructions stored in the memory 102.

The processor 700 may be communicatively coupled with one or more operator interfaces 706 and/or control devices 708. The operator interface 706 may include logs of predicted formation fluid properties that are accessible to an operator. The control device 708 may include one or more devices and/or portions thereof that receive control signals for operation based on the estimated properties of the formation fluid. Such control devices 708 may implement changes in depth of the downhole tool 650 within the wellbore 626, adjustments to the pumping pressure of the pump 668, and/or other control functions, perhaps based on obtained, calculated, and/or estimated formation fluid properties.

Figure 34:
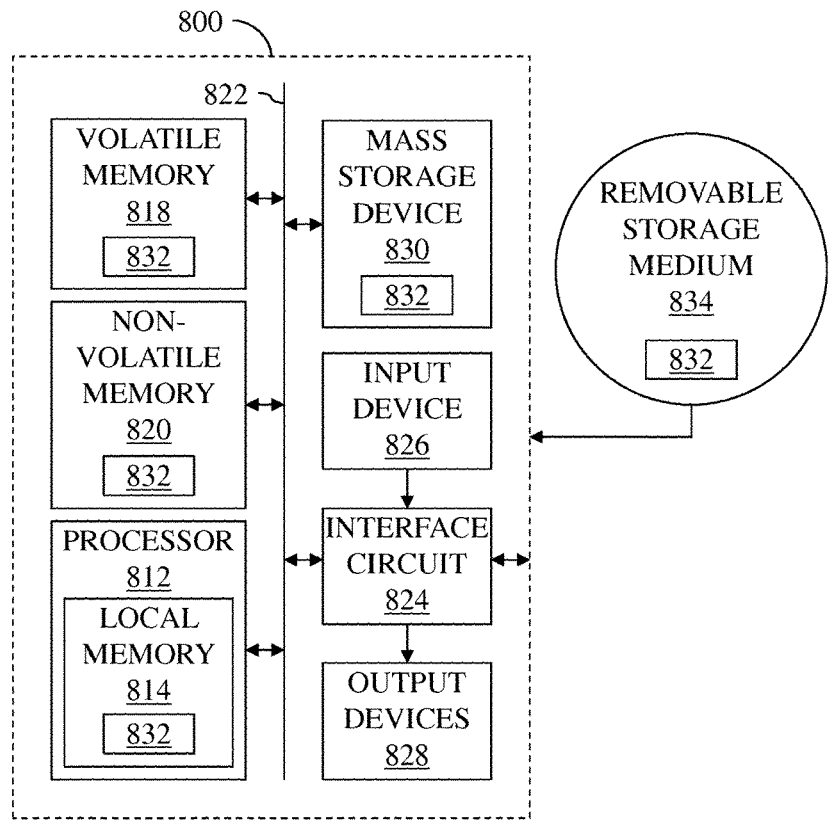
FIG. 34 is a schematic view of at least a portion of an example implementation of apparatus according to one or more aspects of the present disclosure.

FIG. 34 is a schematic view of at least a portion of apparatus according to one or more aspects of the present disclosure. The apparatus is or comprises a processing system 800 that may execute example machine-readable instructions to implement at least a portion of one or more of the methods and/or processes described herein, and/or to implement a portion of one or more of the example downhole tools described herein. The processing system 800 may be or comprise, for example, one or more processors, controllers, special-purpose computing devices, servers, personal computers, personal digital assistant ("PDA") devices, smartphones, internet appliances, and/or other types of computing devices. Moreover, while it is possible that the entirety of the processing system 800 shown in FIG. 34 is implemented within downhole apparatus, such as in the form of at least a portion of the control/monitoring system 690 shown in FIG. 33 and/or other downhole apparatus within the scope of the present disclosure, it is also contemplated that one or more components or functions of the processing system 800 may be implemented in wellsite surface equipment, perhaps including the logging and control equipment 654 depicted in FIG. 31, the surface equipment 656 depicted in FIG. 32, and/or other surface equipment within the scope of the present disclosure.

The processing system 800 may comprise a processor 812 such as, for example, a general-purpose programmable processor. The processor 812 may comprise a local memory 814, and may execute coded instructions 832 present in the local memory 814 and/or another memory device. The processor 812 may execute, among other things, machine-readable instructions or programs to implement the methods and/or processes described herein. The programs stored in the local memory 814 may include program instructions or computer program code that, when executed by an associated processor, enable surface equipment and/or downhole controller and/or control system to perform tasks as described herein. The processor 812 may be, comprise, or be implemented by one or a plurality of processors of various types suitable to the local application environment, and may include one or more of general-purpose computers, special-purpose computers, microprocessors, digital signal processors ("DSPs"), field-programmable gate arrays ("FPGAs"), application-specific integrated circuits ("ASICs"), and processors based on a multi-core processor architecture, as non-limiting examples. Of course, other processors from other families are also appropriate.

The processor 812 may be in communication with a main memory, such as may include a volatile memory 818 and a non-volatile memory 820, perhaps via a bus 822 and/or other communication means. The volatile memory 818 may be, comprise, or be implemented by random access memory (RAM), static random access memory (SRAM), synchronous dynamic random access memory (SDRAM), dynamic random access memory (DRAM), RAMBUS dynamic random access memory (RDRAM) and/or other types of random access memory devices. The non-volatile memory 820 may be, comprise, or be implemented by read-only memory, flash memory and/or other types of memory devices. One or more memory controllers (not shown) may control access to the volatile memory 818 and/or the non-volatile memory 820.

The processing system 800 may also comprise an interface circuit 824. The interface circuit 824 may be, comprise, or be implemented by various types of standard interfaces, such as an Ethernet interface, a universal serial bus (USB), a third generation input/output (3GIO) interface, a wireless interface, and/or a cellular interface, among others. The interface circuit 824 may also comprise a graphics driver card. The interface circuit 824 may also comprise a communication device such as a modem or network interface card to facilitate exchange of data with external computing devices via a network (e.g., Ethernet connection, digital subscriber line ("DSL"), telephone line, coaxial cable, cellular telephone system, satellite, etc.).

One or more input devices 826 may be connected to the interface circuit 824. The input device(s) 826 may permit a user to enter data and commands into the processor 812. The input device(s) 826 may be, comprise, or be implemented by, for example, a keyboard, a mouse, a touchscreen, a track-pad, a trackball, an isopoint, and/or a voice recognition system, among others.

One or more output devices 828 may also be connected to the interface circuit 824. The output devices 828 may be, comprise, or be implemented by, for example, display devices (e.g., a liquid crystal display or cathode ray tube display (CRT), among others), printers, and/or speakers, among others.

The processing system 800 may also comprise one or more mass storage devices 830 for storing machine-readable instructions and data. Examples of such mass storage devices 830 include floppy disk drives, hard drive disks, compact disk (CD) drives, and digital versatile disk (DVD) drives, among others. The coded instructions 832 may be stored in the mass storage device 830, the volatile memory 818, the non-volatile memory 820, the local memory 814, and/or on a removable storage medium 834, such as a CD or DVD. Thus, the modules and/or other components of the processing system 800 may be implemented in accordance with hardware (embodied in one or more chips including an integrated circuit such as an application specific integrated circuit), or may be implemented as software or firmware for execution by a processor. For example, in the case of firmware or software, the embodiment can be provided as a computer program product including a computer readable medium or storage structure embodying computer program code (i.e., software or firmware) thereon for execution by the processor.

Figure 35:
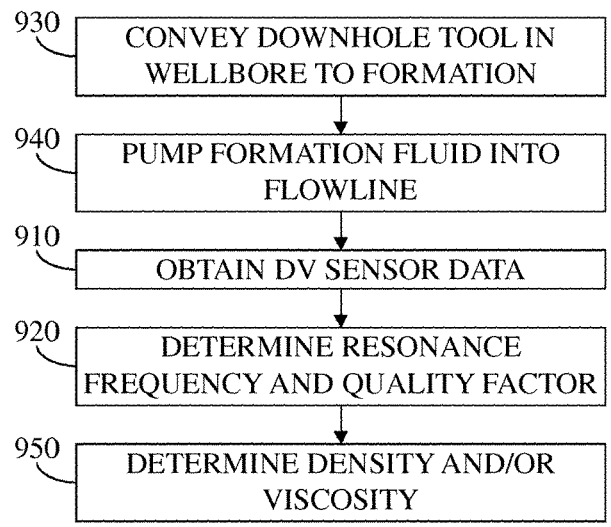
FIG. 35 is a flow-chart diagram of at least a portion of a method according to one or more aspects of the present disclosure.

FIG. 35 is a flow-chart diagram of at least a portion of a method (900) according to one or more aspects of the present disclosure. The method (900) comprises obtaining (910) data from a density-viscosity (DV) sensor of a downhole tool, wherein the DV sensor comprises a resonating element disposed in a fluid flowing in a flowline of the downhole tool. For example, the DV sensor may be or resemble the DV sensors 100-104 shown in one or more of FIGS. 1-12, and the downhole tool may be or resemble one or more of the LWD and/or MWD modules or tools 640, 642 shown in FIG. 31, the downhole tool 650 shown in FIG. 32, and/or other downhole tools within the scope of the present disclosure.

The method (900) also comprises determining (920) a resonance frequency and quality factor of the resonating element of the DV sensor based a primary resonance mode and a secondary resonance mode exhibited in the obtained (910) data. As described above, the secondary resonance mode may exist because it has a resonance frequency that is within a bandwidth of an excitation pulse utilized in obtaining the data. As also described above, the primary resonance mode may be a transverse mode and the secondary resonance mode may be a lateral mode.

Determining (920) the resonance frequency and quality factor may utilize Equation (3) or (3.1) set forth above. However, determining the resonance frequency and quality factor may include determining background drift and offset. In such implementations, determining (920) the resonance frequency, quality factor, background drift, and offset may utilize Equation (4) or (4.1) set forth above.

Determining (920) the resonance frequency and quality factor may utilize a least-squares fitting method, such as a chi-squared ($\chi^2$) method. For example, determining (920) the resonance frequency and quality factor may utilize a nonlinear fitting or regression in which inputs include voltage data from the obtained (910) data and outputs include the resonance frequency, quality factor, and other variables.

The method (900) may also comprise, before obtaining (910) the data, conveying (930) the downhole tool within a wellbore that extends into a subterranean formation, and operating (940) the downhole tool to pump the fluid from the subterranean formation into the flowline and, thus, past the resonating element. The method (900) may also comprise estimating and/or otherwise determining (950) the density and/or viscosity of the formation fluid utilizing the determined (920) resonance frequency and quality factor. For example, determining (950) the density and/or viscosity may utilize one or more of Equations (9)-(11) set forth above.

In view of the entirety of the present disclosure, including the figures and the claims, a person having ordinary skill in the art should readily recognize that the present disclosure introduces a method comprising: obtaining data from a density-viscosity (DV) sensor of a downhole tool, wherein the DV sensor comprises a resonating element disposed in a fluid flowing in a flowline of the downhole tool; and determining a resonance frequency and quality factor of the resonating element based on a primary resonance mode and a secondary resonance mode exhibited in the obtained data.

Obtaining data from the DV sensor may comprise obtaining first data pertaining to the primary resonance mode and subsequently obtaining second data pertaining to the secondary resonance mode. Obtaining data from the DV sensor may comprise simultaneously obtaining first data pertaining to the primary resonance mode and second data pertaining to the secondary resonance mode.

The secondary resonance mode may exist because it has a resonance frequency that is within a bandwidth of an excitation pulse utilized in obtaining the data.

The primary resonance mode may be a transverse mode and the secondary resonance mode may be a lateral mode. Determining the resonance frequency and quality factor may utilize Equation (3) or (3.1) set forth above. Determining the resonance frequency and quality factor may include determining a background drift and offset. Determining the resonance frequency, quality factor, background drift, and offset may utilize Equation (4) or (4.1) set forth above.

Determining the resonance frequency and quality factor may utilize a least-squares fitting method. Determining the resonance frequency and quality factor may utilize a model accounting for the primary and secondary resonance modes, and may involve minimization of a chi-squared ($\chi^2$) statistic determined from the obtained data and the model.

Determining the resonance frequency and quality factor may utilize a nonlinear regression in which inputs may include voltage data from the obtained data and outputs may include the resonance frequency and quality factor.

The method may further comprise, before obtaining the data: conveying the downhole tool within a wellbore that extends into a subterranean formation; and operating the downhole tool to pump the fluid from the subterranean formation into the flowline.

The method may further comprise determining the density and/or viscosity of the fluid utilizing the determined resonance frequency and quality factor.

The present disclosure also introduces an apparatus comprising: a downhole tool operable within a wellbore extending from a wellsite surface into a subterranean formation, wherein the downhole tool comprises: a flowline for conducting fluid obtained from the subterranean formation via operation of the downhole tool; and a density-viscosity (DV) sensor comprising a resonating element disposed in the flowline; and surface equipment disposed at the wellsite surface and in communication with the downhole tool, wherein at least one of the downhole tool and the surface equipment is operable to: obtain data from the DV sensor; and determine a resonance frequency and quality factor of the resonating element based a primary resonance mode and a secondary resonance mode exhibited in the obtained data.

The secondary resonance mode may exist because it has a resonance frequency that is within a bandwidth of an excitation pulse utilized in obtaining the data.

The primary resonance mode may be a transverse mode and the secondary resonance mode may be a lateral mode.

Determining the resonance frequency and quality factor may utilize Equation (3) or (3.1) set forth above. Determining the resonance frequency and quality factor may include determining a background drift and offset. Determining the resonance frequency, quality factor, background drift, and offset may utilize Equation (4) or (4.1) set forth above.

Determining the resonance frequency and quality factor may utilize a least-squares fitting method. Determining the resonance frequency and quality factor may utilize a model accounting for the primary and secondary resonance modes, and may involve minimization of a chi-squared ($\chi^2$) statistic determined from the obtained data and the model.

Determining the resonance frequency and quality factor may utilize a nonlinear regression in which inputs may include voltage data from the obtained data and outputs may include the resonance frequency and quality factor.

At least one of the downhole tool and the surface equipment may be operable to determine the density and/or viscosity of the fluid utilizing the determined resonance frequency and quality factor.

The present disclosure also introduces a method comprising: obtaining data from a density-viscosity (DV) sensor of a downhole tool, wherein the DV sensor comprises a resonating element disposed in a fluid flowing in a flowline of the downhole tool; and determining from the obtained data a resonance frequency and quality factor of the resonating element utilizing a nonlinear regression.

Inputs for the nonlinear regression may include voltage data from the obtained data and outputs may include the resonance frequency and quality factor.

The nonlinear regression may utilize a model accounting for at least one resonance mode. The nonlinear regression may utilize a least-squares fitting method. The least-squares fitting method may involve minimization of a chi-squared ($\chi^2$) statistic determined from the obtained data and the model. The model may utilize Equation (1) set forth above. The at least one resonance mode may include a plurality of resonance modes, and the model may utilize Equation (3.1) or (4.1) set forth above.

The method may further comprise determining the density and/or viscosity of the fluid utilizing the determined resonance frequency and quality factor.

The foregoing outlines features of several embodiments so that a person having ordinary skill in the art may better understand the aspects of the present disclosure. A person having ordinary skill in the art should appreciate that they may readily use the present disclosure as a basis for designing or modifying other processes and structures for carrying out the same functions and/or achieving the same benefits of the embodiments introduced herein. A person having ordinary skill in the art should also realize that such equivalent constructions do not depart from the spirit and scope of the present disclosure, and that they may make various changes, substitutions and alterations herein without departing from the spirit and scope of the present disclosure.

The Abstract at the end of this disclosure is provided to comply with 37 C.F.R. § 1.72(b) to permit the reader to quickly ascertain the nature of the technical disclosure. It is submitted with the understanding that it will not be used to interpret or limit the scope or meaning of the claims.

What is claimed is:

1. A method, comprising:
deploying a downhole tool into a wellbore, said downhole tool comprises a density viscosity (DV) sensor having a resonating element disposed in a flowline of the downhole tool;
exciting the density viscosity (DV) sensor and obtaining data corresponding to a first resonance mode and a second resonance mode during a flow of a fluid in the flowline of the downhole tool;
in a processor, fitting the data to an equation, wherein the equation comprises a first term corresponding to the first resonance mode and a second term corresponding to the second resonance mode; and
in the processor, determining, based at least in part on the equation, a first resonance frequency and a first quality factor of the resonating element in the fluid corresponding to the first resonance mode and a second resonance frequency and a second quality factor of the resonating element in the fluid corresponding to the second resonance mode, wherein the first resonance frequency, the first quality factor, the second resonance frequency, and the second quality factor are indicative of properties of the fluid.

2. The method of claim 1 wherein the equation comprises a general form of:

$$v(t)=A_1 e^{-\alpha_1 107\,1t}\sin(\omega_1 t+\phi_1)+A_2 e^{-\alpha_2 107\,2t}\sin(\omega_2 t+\phi_2)$$

where $A_1$ is amplitude of a first initial transient relative to the first resonance mode, $\alpha_1$ is logarithmic decrement controlling damping of motion of the resonating element relative to the first resonance mode, $\omega_1$ is the first resonance frequency of the resonating element, t is a time index, $\phi_1$ is phase angle relative to the first resonance mode, $A_2$ is amplitude of a second initial transient relative to the second resonance mode, $\alpha_2$ is logarithmic decrement controlling damping of motion of the resonating element relative to the second resonance mode, $\omega_2$ is the second resonance frequency of the resonating element, and $\phi_2$ is phase angle relative to the second resonance mode.

3. The method of claim 1 comprising determining a background drift and an offset, wherein the background drift comprises time-drift.

4. The method of claim 3 wherein the equation comprises a general form of:

$$v(t) = A_1 e^{-\alpha_1 \omega_1 t} \sin(\omega_1 t + \phi_1) + A_2 e^{-\alpha_2 \omega_2 t} \sin(\omega_2 t + \phi_2) + A_3 e^{-\sigma t} + a$$

where $A_1$ is amplitude of a first initial transient relative to the first resonance mode, $\alpha_1$ is logarithmic decrement controlling damping of motion of the resonating element relative to the first resonance mode, $\omega_1$ is the first resonance frequency, t is a time index, $\phi_1$ is phase angle relative to the first resonance mode, $A_2$ is amplitude of a second initial transient relative to the second resonance mode, $\alpha_2$ is logarithmic decrement controlling damping of motion of the resonating element relative to the second resonance mode, $\omega_2$ is the second resonance frequency, $\phi_2$ is phase angle relative to the second resonance mode, $A_3$ and $\sigma$ account for the time-drift due to unknown background interference, and a is an additional unknown constant that characterizes the offset.

5. The method of claim 1 wherein fitting the data to the equation utilizes a least-squares fitting method.

6. The method of claim 5 wherein utilizing the least-squares fitting method comprises minimization of a chi-squared ($\chi^2$) statistic determined from the obtained data and the equation.

7. The method of claim 1 wherein fitting the equation utilizes a nonlinear regression in which inputs include voltage data from the obtained data and outputs include the first resonance frequency and the first quality factor.

8. The method of claim 7 wherein the nonlinear regression utilizes the equation, wherein the equation accounts for at least two resonance modes.

9. The method of claim 8 wherein the at least two resonance modes includes a number n of resonance modes, wherein n is greater than or equal to two, and wherein the equation has a general form of:

$$v(t) = \sum_{i=1}^{i=n} A_i e^{-\alpha_i \omega_i t} \sin(\omega_i t + \phi_i)$$

where $A_i$ is amplitude of an initial transient relative to the $i^{th}$ resonance mode, $\alpha_i$ is logarithmic decrement controlling damping of motion of the resonating element relative to the $i^{th}$ resonance mode, $\omega_i$ is resonance frequency of the resonating element relative to the $i^{th}$ resonance mode, t is a time index, and $\phi_i$ is phase angle relative to the $i^{th}$ resonance mode.

10. The method of claim 8 wherein the at least two resonance modes includes a number n of resonance modes, wherein n is greater than or equal to two, and wherein the equation has a general form of:

$$v(t) = \sum_{i=1}^{i=n} A_i e^{-\alpha_i \omega_i t} \sin(\omega_i t + \phi_i) + B e^{-\sigma t} + a$$

where $A_i$ is amplitude of an initial transient relative to the $i^{th}$ resonance mode, $\alpha_i$ is logarithmic decrement controlling damping of motion of the resonating element relative to the $i^{th}$ resonance mode, $\omega_i$ is resonance frequency of the resonating element relative to the $i^{th}$ resonance mode, t is a time index, $\phi_i$ is phase angle relative to the $i^{th}$ resonance mode, B and $\sigma$ account for time-drift due to unknown background interference, and a is an additional unknown constant that characterizes offset.

11. The method of claim 1, wherein the properties of the fluid are at least one of density and viscosity of the fluid, and further comprising determining at least one of the density and the viscosity of the fluid based at least in part on the first resonance frequency or the first quality factor.

12. The method of claim 1 wherein exciting the DV sensor comprises exciting the DV sensor via a first excitation and the data is first data, wherein the method further comprises exciting the DV sensor via a second excitation and obtaining second data corresponding to the first resonance mode and the second resonance mode.

13. The method of claim 12 wherein the first excitation is a transverse excitation and the second excitation is a lateral excitation or vice versa.

14. The method of claim 1 wherein the equation comprises a third term corresponding to a background drift or an offset, wherein the third term comprises an exponential.

15. An apparatus, comprising:
a downhole tool operable within a wellbore extending from a wellsite surface into a subterranean formation, wherein the downhole tool comprises:
a flowline for conducting fluid obtained from the subterranean formation via operation of the downhole tool;
a density-viscosity (DV) sensor comprising a resonating element disposed in the flowline; and
surface equipment disposed at the wellsite surface and in communication with the downhole tool, wherein at least one of the downhole tool and the surface equipment comprises a processor operable to:
receive electrical signals corresponding to a movement of the resonating element;
fit the movement of the resonating element to an equation, wherein the equation comprises a first term corresponding to a first resonance mode and a second term corresponding to a second resonance mode; and
determine a resonance frequency and a quality factor of the resonating element in the fluid for each of the first resonance mode and the second resonance mode, wherein the resonance frequency and the quality factor are indicative of properties of the fluid.

16. The apparatus of claim 15 wherein to fit the movement of the resonating element to the equation utilizes a nonlinear regression.

17. The apparatus of claim 16 wherein the nonlinear regression utilizes a least-squares fitting method.

18. The apparatus of claim 17 wherein the least-squares fitting method involves minimization of a chi-squared ($\chi^2$) statistic corresponding to the received electrical signals and the equation.

19. The apparatus of claim 15 wherein the properties of the fluid are at least one of density and viscosity of the fluid, and wherein at least one of the downhole tool and the surface equipment is operable to determine at least one of the density and the viscosity of the fluid utilizing the determined resonance frequency and quality factor.

20. The apparatus of claim 15 wherein the received electrical signals comprise voltage data corresponding to the movement of the resonating element.

* * * * *